United States Patent
Foster et al.

(10) Patent No.: US 6,505,079 B1
(45) Date of Patent: Jan. 7, 2003

(54) ELECTRICAL STIMULATION OF TISSUE FOR THERAPEUTIC AND DIAGNOSTIC PURPOSES

(75) Inventors: George B. Foster, Columbus, OH (US); Thomas L. Fletcher, Columbus, OH (US)

(73) Assignee: Foster Bio Technology Corp., Columbus, OH (US)

( * ) Notice: Subject to any disclaimer, the term of this patent is extended or adjusted under 35 U.S.C. 154(b) by 23 days.

(21) Appl. No.: 09/661,068

(22) Filed: Sep. 13, 2000

(51) Int. Cl.[7] .................................................. A61N 1/18

(52) U.S. Cl. .............................. 607/68; 607/63; 607/72; 607/74

(58) Field of Search .............................. 607/45, 63, 68, 607/70, 72, 74

(56) References Cited

U.S. PATENT DOCUMENTS

| | | | |
|---|---|---|---|
| 3,835,833 A | | 9/1974 | Limoge |
| 4,177,819 A | * | 12/1979 | Kofsky et al. ................. 607/63 |
| 4,363,324 A | * | 12/1982 | Kusserow ..................... 607/63 |
| 5,269,302 A | * | 12/1993 | Swartz et al. .................. 607/63 |
| 5,470,347 A | * | 11/1995 | Swartz et al. .................. 607/45 |
| 6,014,587 A | * | 1/2000 | Shaw et al. .................... 607/45 |

OTHER PUBLICATIONS

Champagne, C., Papiernik, E., Thierry, J.P., and Noviant, Y., Transcutaneous cranial electrical stimulation by Limoge currents during labor, Ann. Fr. Anesth. Reanim., Masson, Paris, 1984.

Ellison, F., Ellison, W., Daulouede, J. P., Daubech, F. E., Pautrizel, B., Bourgeois, M. and Tignol, J., Opiate withdrawal and electrostimulation double blind experiments, Encephale, 13 (1987) 225–229.

Limoge, A., An introduction to elecrtoanaesthsia. In: R.M. Johnson (Ed.), University Park Press, Baltimore, MD, 1975, pp. 1–121.

Limoge, A., Louville, Y., Barritault, L., Cazalaa, J.B. and Atinault, A., Electrical anesthesia. In: J. Spierdijk, S.A. Feldman, H. Mattie and T.H. Stanley (Eds.), Developments in Drug Used in Anesthesia, Leiden University Press, Leiden, 1981, pp. 121–134.

Limoge, A. and Boisgontier, M.T., Characteristic of electric currents used in human anesthesiology. In: B. Rybak (Ed.), Advanced Technology, Sijthoff and Noordhoff, German–town, 1979, pp. 437–446.

(List continued on next page.)

Primary Examiner—Jeffrey R. Jastrzab
(74) Attorney, Agent, or Firm—Mueller and Smith, LPA

(57) ABSTRACT

Electrobiological stimulation is carried out transcranially by applying high frequency squarewave bursts exhibiting no d.c. term across the cranial region. Such stimulation is commenced employing ramp generators and positive and negative voltage converters which evolve the requisite baseform and burst frequencies having a voltage waveform which is square in nature. Both voltage and current are sensed and subjected to comparator logic in conjunction with predetermined thresholds and windows. Overcurrent detection and overvoltage detection is provided in hard wired fashion to assure rapid shutdown response. D.C offset detection is provided along with waveform balance tests to further assure the safety of the system. Diagnostic procedures as well as therapeutic procedures may be carried out with a system version which provides for the application of a stimulus in conjunction with safety monitoring and controller based development of stimulating waveforms, all of which exhibits no d.c. term. Feed point voltage waveforms and current waveforms are mathematically processed and compared for diagnostic analysis.

9 Claims, 18 Drawing Sheets

OTHER PUBLICATIONS

Stanley, T.H., Cazalaa, J.A., Atinault, A., Coeytaux, R., Limoge, A. and Louville, Y., Transcutaneous cranial electrical stimulation decreases narcotic requirements during neuroleptic anesthesia and operation in man, Anest. Analg., 61 (1982) 863–866.

Stanley, T.H., Cazalaa, J.A., Limoge, A. and Louville, Y., Transcutaneous cranial electrical stimulation increases the potency of nitrous oxide in humans, Anesthesiology, 57 (1982) 293–297.

* cited by examiner

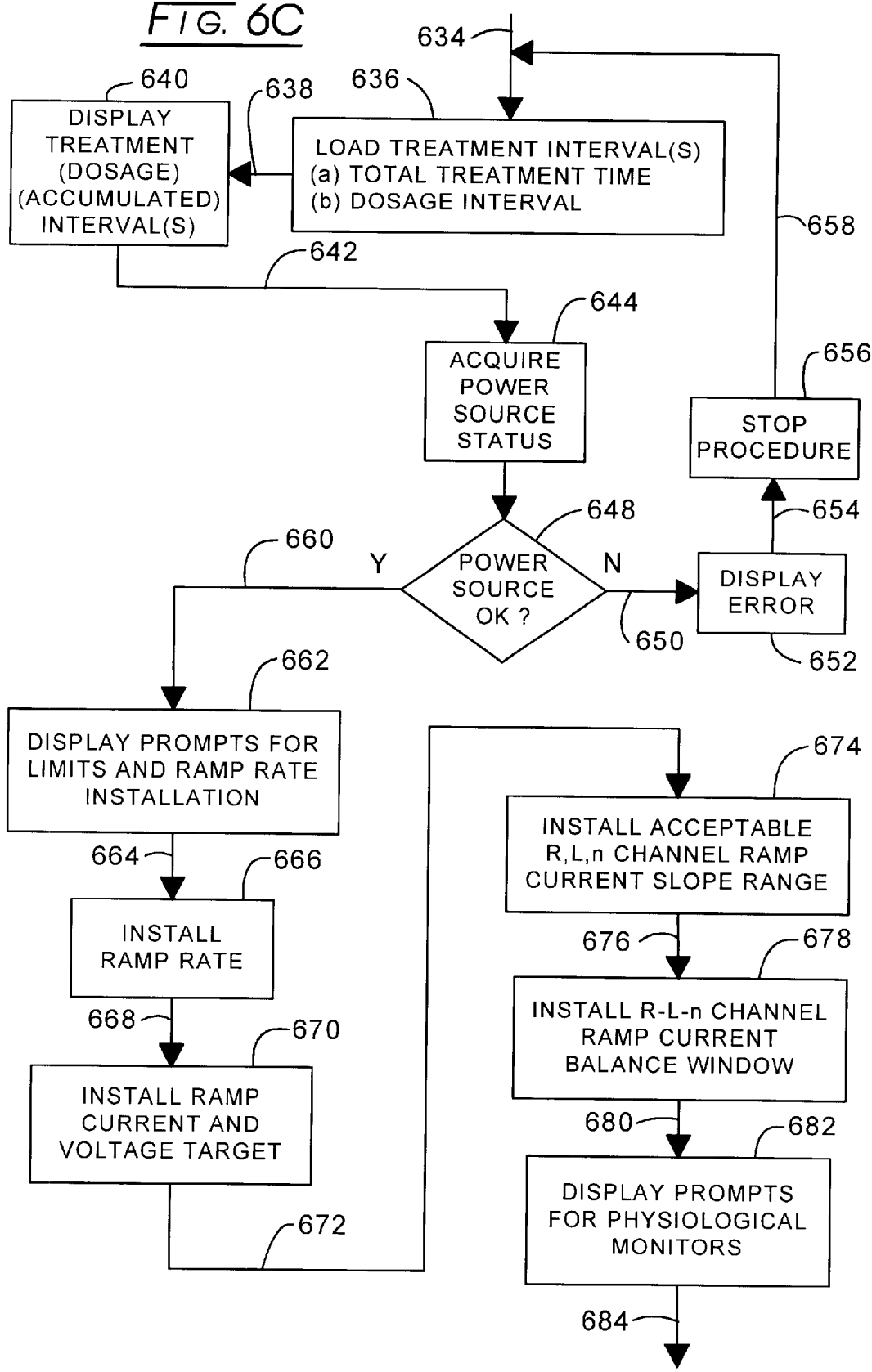

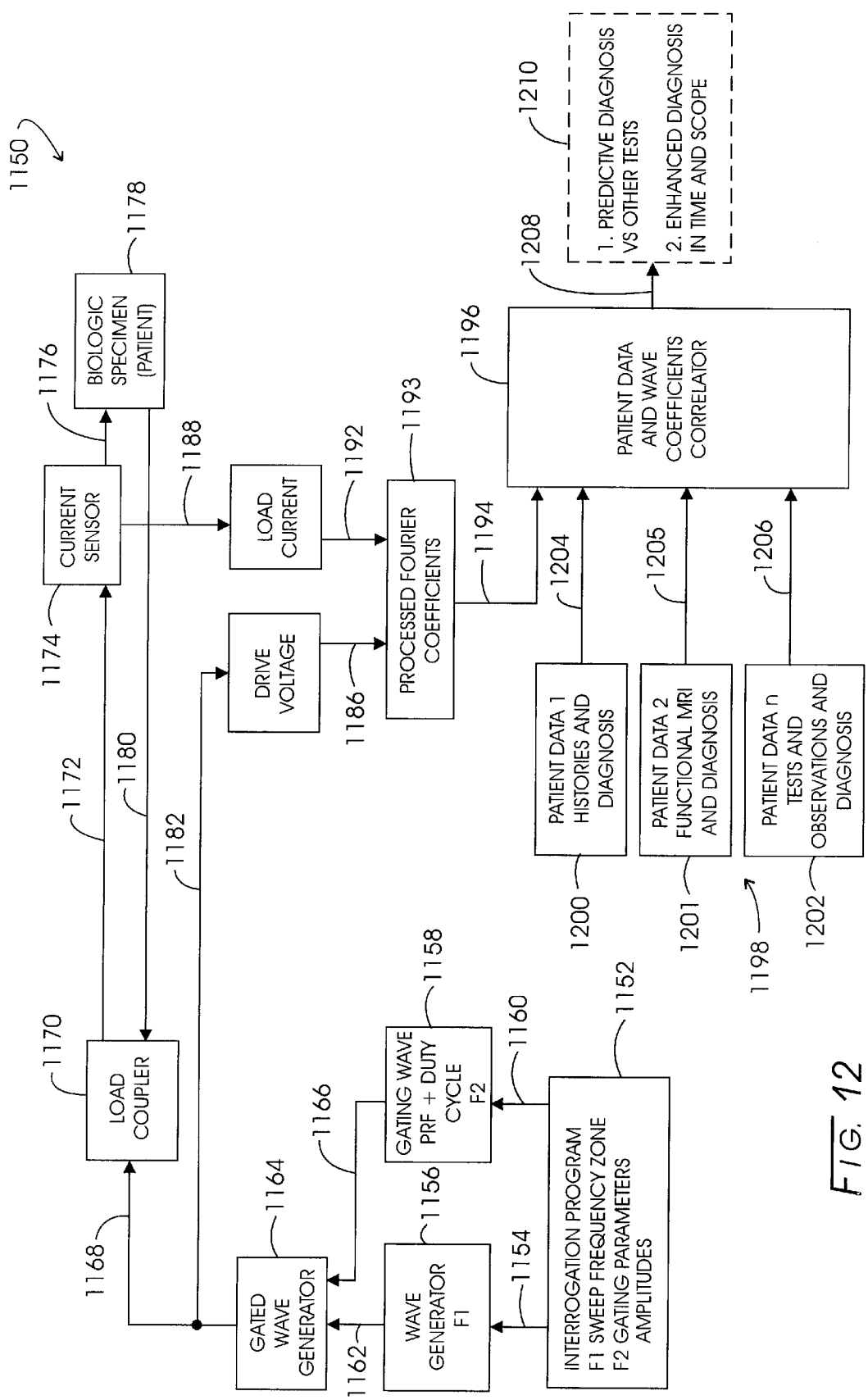

ELECTRICAL STIMULATION OF TISSUE FOR THERAPEUTIC AND DIAGNOSTIC PURPOSES

CROSS-REFERENCE TO RELATED APPLICATIONS

STATEMENT REGARDING FEDERALLY SPONSORED RESEARCH

Not applicable.

BACKGROUND OF THE INVENTION

Alternative medicine approaches to the treatment of a variety of physical and mental conditions have been the subject of substantial investigation and interest. See: Journal of the American Medical Association (1998), 280 (18). Nontraditional techniques in the management of pain have ranged from classic acupuncture to the electrical stimulation of tissue. In the latter regard, the efficacy of electrical stimulation from skin surface attached electrodes have been the subject of a substantial amount of investigation. Referred to generally as transcutaneous electrical nerve stimulation (TENS), typically a relatively low level of current, for example, in the milliamp range which is manifested as a squarewave is introduced to some select region of the peripheral nervous system for a prescribed treatment interval. The frequency of this squarewave signal is relatively low, ranging generally from a few Hertz to about 100 Hertz and patient response to the application of such low frequency currents at the skin has been described as an unpleasant experience.

Somewhat recently, a combination of electrical stimulation and acupuncture has evolved. This technique differs from traditional acupuncture in that the needle itself is not the focus of treatment, instead, it serves as a conductor of electricity. One approach with electroacupuncture has been described as percutaneous electrical nerve stimulation (PENS). This PENS therapy utilizes acupuncture-like needle probes positioned in the soft tissue to stimulate peripheral sensory nerves at the dermatomal levels.

In the 1970s, Limoge, working in France, evolved an electroanesthesia electroanalgesia approach involving a different form of stimulation sometimes referred to as "Limoge currents" wherein, for example, a pulse cycle comprising pulses consisting of a positive wave for $2 \mu S$ is followed by a negative wave of $4 \mu S$. The group has a period duration of $6 \mu S$ corresponding to 166 kHz. These groups have been referred to as bi-phasic balanced currents. They are gated on for four milliseconds followed by an off period of six milliseconds. The total cycle period thus is ten milliseconds corresponding to a 100 Hz gating cycle or burst frequency.

The integrals of the positive high frequency pulses and the negative high frequency pulses are maintained in balance. This results in a zero net applied current and eliminates or substantially abates a potential for electrophoresis. The current intensity generally will be from about 220 mA to about 250 mA peak to peak. In general, application of the current is by transcranial electrical stimulation (TCES) which is applied to the head through a frontal electrode and two posterior electrodes at the level of the mastoid bones. TCES treatment evidences no apparent side effects and has been used with very positive results in abdominal, urological gynecolgical and orthopedic surgery and traumatology and in addiction withdrawal therapy. TCES has been shown to enhance the potency of conventional pharmaceuticals during surgery and to evoke a reduction in the need for opiate analgesic during neuroleptanalgesia. Mathematical analysis of the Limoge currents indicates that the use of high frequency currents allow deep penetration of the electric field into the brain. It has been thought that the dielectric properties of biological tissue enables, in situ, the high frequency current combination with low frequency currents is responsible for the analgesic potentiaton. See the following publications:

Limoge, A., An introduction to electroanaesthsia. In: R. M. Johnson (Ed.), University Park Press, Baltimore, Md., 1975, pp. 1–121.

Limoge, A., Louville, Y., Barritault, L., Cazalaa, J. B. and Atinault, A., Electrical anesthesia. In: J. Spierdijk, S. A. Feldman, H. Mattie and T. H. Stanley (Eds.), Developments in Drug Used in Anesthesia, Leiden University Press, Leiden, 1981, pp. 121–134.

Limoge, A. and Boisgontier, M. T., Characteristic of electric currents used in human anesthesiology. In: B. Rybak (Ed.), Advanced Technology, Sijthoff and Noordhoff, German-town, 1979, pp. 437–446.

Champagne, Papiemak, Thierry, and Noviant, Transcutaneous Cranial Electrical Stimulation by Limoge Currents During Labor, Ann. Fr. Anesth. Reanim., Masson Paris, 1984.

Stanley, T. H., Cazalaa, J. A., Atinault, A., Coeytaux, R., Limoge, A. and Louville, Y., Transcutaneous cranial electrical stimulation decreases narcotic requirements during neuroleptic anesthesia and operation in man, Anest. Analg., 61 (1982) 863–866.

Stanley, T. H., Cazalaa, J. A., Limoge, A. and Louville, Y., Transcutaneous cranial electrical stimulation increases the potency of nitrous oxide in humans, Anesthesiology, 57 (1982) 293–297.

Ellison, F., Ellison, W., Daulouede, J. P., Daubech, F. E., Pautrizel, B., Bourgeois, M. and Tignol, J., Opiate withdrawal and electrostimulation double blind experiments, Encephale, 13 (1987) 225–229.

In support of an expanded utilization of the Limoge currents in the control and management of pain and a variety of medical conditions, investigators and practitioners now find need for improved generation equipment with heightened capacities for investigation of variations of the Limoge current signatures or characteristics and for utilization of these variations and their effect for diagnostic applications to treatment as well as therapeutic purposes.

BRIEF SUMMARY OF THE INVENTION

The present invention is addressed to the subject of electrobiological stimulation. It particularly is directed to the introduction of systems, devices and methods which not only support current therapeutic techniques of electrostimulation considered effective, but also provide investigators, including research clinicians, with a support system permitting enhanced research endeavors.

The system has been evolved with a recognition that an electrical waveform can be applied to a load, here tissue, exhibiting variable and unknown electrical impedance characteristics in a manner wherein those electrical characteristics can be analyzed. Those electrical characteristics will correspond with the tissue characteristics of the material constituting such load. For the present investigatory system, that load is the animal head. Expanding upon the electrode stimulation developed by Limoge (TCES) the present system exhibits enhanced procedures and efficiencies for carrying out now established therapeutic protocols. As an adjunct to these features, the system and technique provide apparatus and method with capabilities for supporting both patient stimulation as well as diagnosis and clinical research in electrobiological stimulation technologies. In the latter regard, the instant approach recognizes that rectangular wave comprising high frequency harmonics of base frequency signals with positive-going and negative-going features are combined to exhibit no d.c. term. In general, the ultimately derived waveforms are assembled by gating at a burst frequency. However, when said high frequency is applied to a biological load such as a human head, a resultant current waveform, when compared to the corresponding applied or feed point voltage waveform, will exhibit aberrations representing, for example, impedance characteristics of the cranial region through which current passes. Digitization and analysis of these two waveforms evolves valuable diagnostic data. Such analysis will include Fourier transform definition of both waveforms in conjunction with mathematical analyses thereof which manipulate data representing their differences. Laplace-mathematical operators also provide substantial analysis of the impedance characteristics throughout the region coursed by one or more channels of current flow. As is apparent, as such analysis is applied to an expanding patient population, an important database can be evolved with a library of accessible mathematical parameters, biological parameters and symptom parameters to evoke expanding diagnostic possibilities and accuracies. Thus, the apparatus, system and method of the invention is directed to providing practitioners and researchers an improved therapeutic capability coupled with a unique diagnostic opportunity.

In one embodiment, apparatus is provided for applying current for therapeutic purpose which incorporates a control assembly. That control assembly performs in conjunction with positive and negative voltage converters operating in two channels, as well as a network of voltage and current monitors. The control assembly determines impedance values for each channel and carries out comparison procedures to evaluate not only that impedance, but peak values of voltage and current, overvoltage and overcurrent conditions, and channel balance conditions. Where those operational parameters are beyond specified limits, the apparatus is automatically shutdown. Detection of any d.c. term greater than some limit and resultant shutdown also is made for the safety of the patient.

In another embodiment, a controller is provided which affords the practitioner substantial versatility and waveshape structuring, a feature particularly valuable for carrying out a variety of electrobiologic diagnostic procedures. This controller mathematically processes monitored voltage and current at the feedpoint electrodes to derive a broad variety of electrically defined biological factors. Memory is employed not only to retain such data but also to provide a library of similar data derived from patient populations.

As another feature, the invention provides a method for applying an electrical stimulus transcranially to an animal with skin regions located adjacent a volume of tissular material, comprising the steps of:

(a) providing first and second electrode assemblies of respective first and second polarities;

(b) providing electrical generation apparatus electrically coupled with the first and second electrode assemblies, responsive to a generator input to provide an excitation output, across the first and second electrode assemblies at frequencies and with waveshapes exhibiting given electrical characteristics;

(c) providing a current sensor assembly responsive to the electrical excitation outputs for providing a monitored current value output;

(d) providing a voltage sensor assembly responsive to the electrical excitation outputs for providing a monitored voltage value output;

(e) providing a controller having a memory and a display and controllable to derive a generator input for producing the excitation output exhibiting predetermined frequencies and waveforms;

(f) electrically coupling the first electrode assembly to the first skin surface region;

(g) electrically coupling the second electrode assembly to a second skin surface region spaced from the first skin surface region;

(h) controlling the controller to derive a generator input to produce an excitation output across the tissular volume for a predetermined application interval, such excitation output having electrical characteristics defining the waveform with positive-going and negative-going waveform components combined to exhibit substantially no d.c. term and occurring at a base frequency value and at a burst repetition frequency value less than the base frequency value;

(i) controlling the controller to record in the memory, the monitored voltage output as voltage data corresponding with the electrical characteristic; and (j) controlling the controller to record in the memory the monitored current output in correspondence with the monitored voltage output as current data corresponding with the electrical characteristics and influenced by the impedance characteristics extant at the volume of tissular material.

Other objects of the invention will, in part, be obvious and will, in part, appear hereinafter.

The invention, accordingly, comprises the apparatus, system and method possessing the construction, combination of elements, arrangement of parts and steps which are exemplified in the following detailed description.

For a fuller understanding of the nature and objects of the invention, reference should be had to the following detailed description taken in connection with the accompanying drawings.

BRIEF DESCRIPTION OF THE DRAWINGS

FIG. 3A is a schematic representation of a human head with the application of two electrodes at the cranial region, while

FIGS. 6A–6G combine to provide a flowchart describing the operation of the system of FIGS. 5A and 5B;

FIG. 12 is a block schematic diagram representing the functions and components of a diagnostic implementation of the invention.

DETAILED DESCRIPTION OF THE INVENTION

In the discourse to follow, an initial apparatus is described which functions to generate a Limoge signal in terms of a high frequency (167 kHz) where a positive-going waveshape is produced for an interval of two microseconds, followed by a negative-going continuum of one half the absolute value of the positive-going amplitude but for an interval of four microseconds. This high frequency signal thus carries no d.c. term. A zero d.c. term characteristic avoids iontophoresis or damaging salt buildup in the tissue of the patient. This high frequency waveform is produced for a burst interval of four ms ON followed by an OFF interval of 6 ms. Such sequence is repeated at each ten ms interval. In the Limoge constructed devices heretofore in use, the operator of the generator system observes current values at an ammeter and gradually elevates voltage by turning a dial to, in turn, evolve a current value which increases until it reaches a desired current peak-to-peak amplitude which heretofore has been established as 140 milliamps per channel. As that current value is observed, the operator ceases voltage elevation and the treatment is carried out for some prescribed interval, for example, three hours. Two channels are utilized for application of this current. To provide these two channels, two input electrodes are utilized which are applied to the skin surface of the patient at the mastoid region in back of the ear and a return electrode also is applied to the patient at the center of the forehead. In general, a capacitor having a coupling function is utilized in this Limoge system to assure that any d.c. term is avoided. With the initial embodiment shown, a waveform at the noted high frequency is generated with a positive-going amplitude which is twice that of an immediately subsequently occurring negative component, the latter of which has a duration which is twice that of the positive-going component and at an amplitude of one half of the positive going component.

Figure 1:
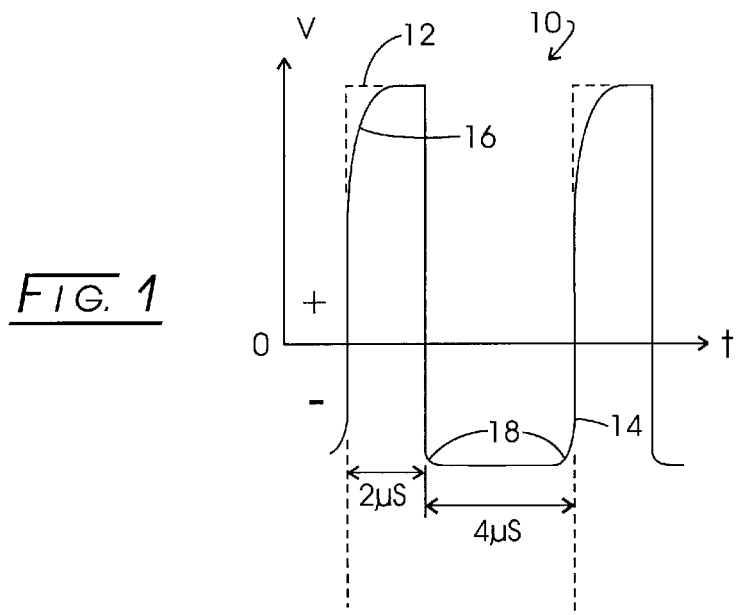
FIG. 1 is a schematic representation of voltage and current waveshapes utilized with the system of the invention.

Looking to FIG. 1, the high frequency aspect of the applied waveform employed with the present invention is represented generally at 10. The squarewave involved is shown at 12, partially in dashed line fashion. This squarewave persists for an interval of two microseconds, whereupon it is continued with the squarewave represented partially in dashed line fashion at 14 as a negative-going component which persists for four microseconds and has an amplitude equal to one half that of the positive-going component 12. Where the current passing from a feed electrode assembly to a return is observed, it will exhibit a rounded or attenuated characteristic. For example, the positive-going component 12 will be rounded as shown at the curve region 16 and the negative going component 14 will be rounded as shown by the solid line curve portion 18.

With the present approach to this waveshape phenomena, it has been determined that the differential or difference between this rounded curve form shown in solid line fashion at 16 and 18 and the applied squarewave will represent inter alia, information or data which will correspond to electrical parameters such as impedance exhibited by the cerebral tissue through which the current passes.

Figure 2:
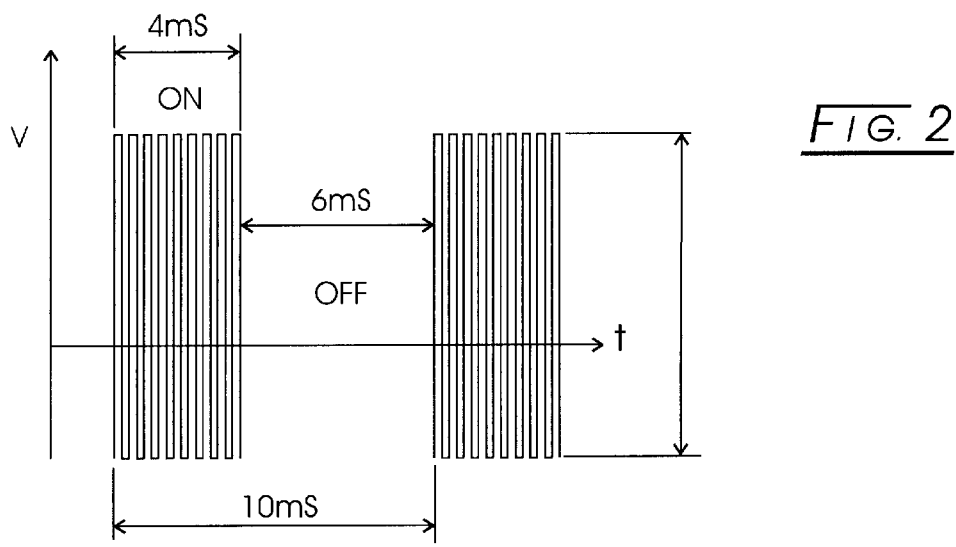
FIG. 2 is a schematic representation of the gated duration of the waveforms of FIG. 1.

FIG. 2 shows the burst characteristics of the signal transmitted through the electrodes. In this regard, the squarewave is produced at high frequency for an interval of four milliseconds and turned off for a succeeding six milliseconds whereupon it again is generated. This provides for a burst or gated pulse commencing each ten milliseconds. The amplitude of this signal generally ranges between 30–50 volts.

Figure 3A:
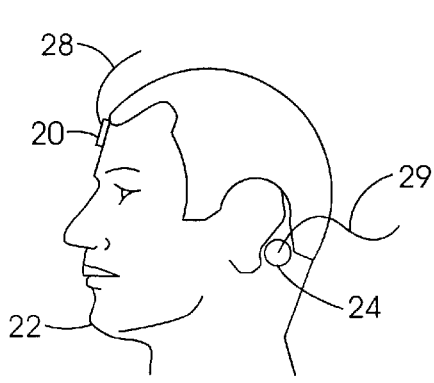
Figure 3B:
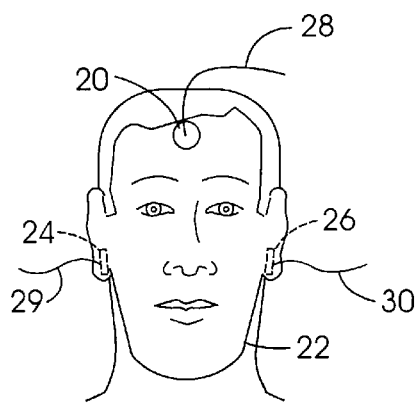
FIG. 3B is a frontal view of the head of FIG. 3A showing the positioning of three electrodes.

Application assemblies or electrodes which are utilized in applying the noted current may take a variety of configurations, for example, electrodes similar to those used with conventional EKG devices have been suggested. However, surface electrodes retained in skin contacting position by a harness-like structure have been found to be beneficial. In general, the devices are utilized in conjunction with an electrical coupling enhancing ointment or the like. In FIGS. 3A and 3B a return electrode is shown at 20 attached to a skin region of the patient 22 located at the forehead. This positioning is between the eyes as seen in FIG. 3B. Two, channel defining input electrodes are positioned against the opposed sternocleido mastoid, i.e., just below the ear. These channel designated electrodes are represented at 24 and 26 in the figures. Leads 28–30 are shown extending from respective electrodes 20, 24 and 26. The leads extend to terminals on the generating apparatus. As is apparent, current passing through the electrode pair 24–20 and electrode pair 26–20 will traverse cranial tissue including the brain. That tissue will exhibit, for example, electrical parameters which include the impedance of that region of current passage.

Figure 4:
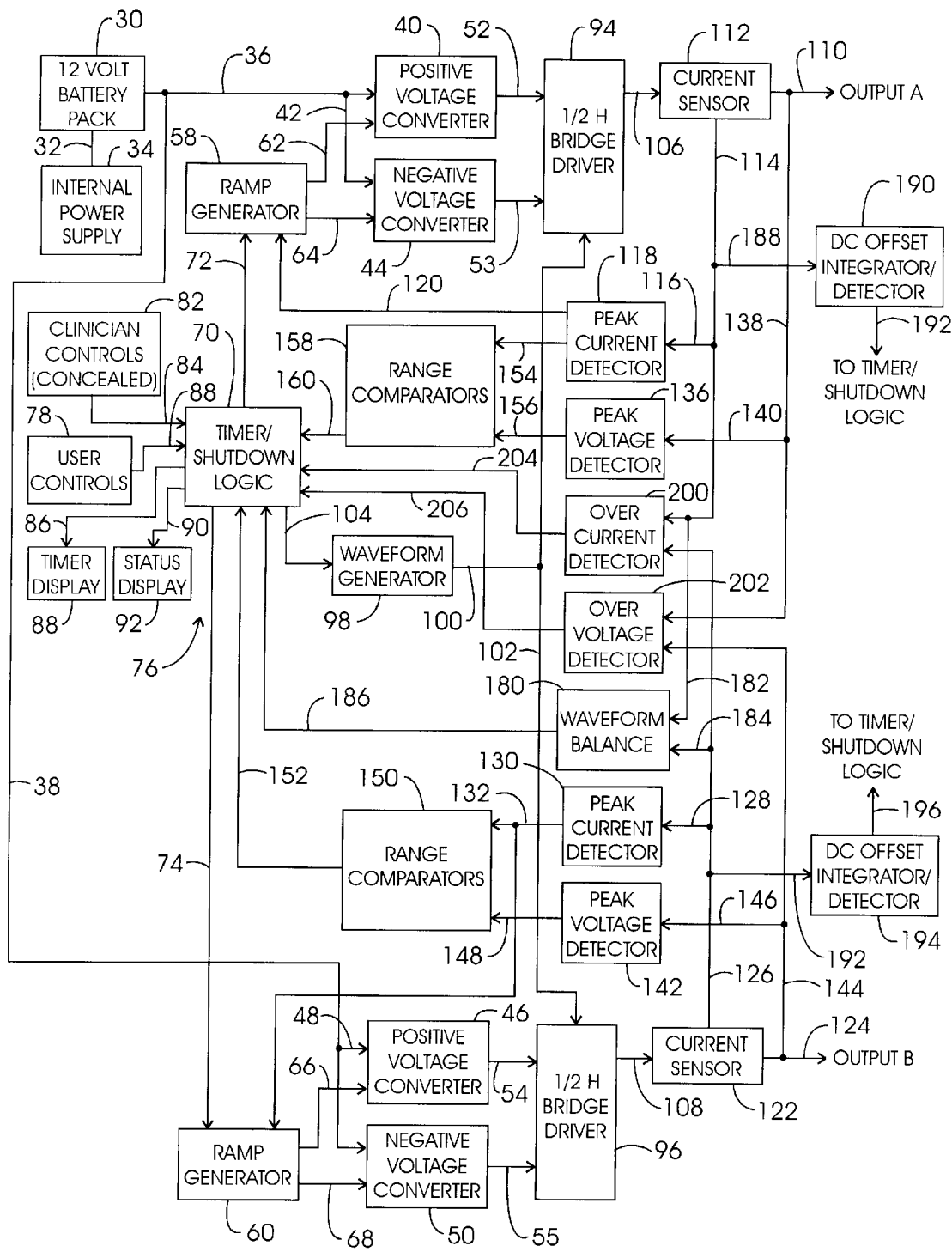
FIG. 4 is an electrical block diagram of one embodiment of apparatus according to the invention.

Now turning to FIG. 4, an initial embodiment of improved generating apparatus for utilization with the electrodes described in connection with FIGS. 3A and 3B is presented. For convenience and safety of application, this equipment is battery powered. In the figure, a 12 volt battery pack is represented at block 30. This battery power supply provides an internal power supply as represented at line 32 and block 34 and, as represented at lines 36 and 38, provides a power input to paired positive and negative voltage converters. These converters establish two channels of excitation output leading to electrodes as described above at 24 and 26. Line 36 provides power input to a positive voltage converter represented at block 40, as well as through line 42 to a negative voltage converter represented at block 44. In similar fashion, line 38 extends from line 36 to the second channel voltage converters. In this regard, lines 38 and 48 are seen directed to the input of a positive voltage converter represented at block 46, while line 38 extends to the input of a negative voltage converter represented at block 50. These voltage converters may be implemented, for example, as switch-mode d. c.—d. c. converters of type ADP108 marketed by Analog Devices, Inc., of Norwood, Mass. At the commencement of a procedure, the d.c. outputs of these converters, as represented at lines 52–55 are gradually increased from 0 voltage to a predetermined therapeutic level, for example, at a ramp rate which is relatively slow, for example, 10 volts per second. Ramp control into the converter pairs for each of the channels is provided by a ramp generator. In this regard, the ramping control over converters 40 and 44 is provided by a ramp generator represented at block 58. Correspondingly, the ramp control of voltage converters 46 and 50 is provided by a ramp generator 60. These control inputs are represented, in the case of ramp generator 58, by lines 62 and 64, while corresponding control inputs from ramp generator 60 are represented at lines 66 and 68. Ramp generators 58 and 60 may be implemented for example, utilizing operational amplifiers of a type LM741 marketed by National Semiconductor Corporation of Santa Clara, Calif. Enablement and starting of the ramp generator control is provided from a Timer/Shutdown logic function represented at block 70, such control with respect to ramp generator 58 being represented at line 72 and corresponding control to ramp generator 60 being represented at line 74. The Timer/Shutdown logic 70 may be implemented with programmable logic devices, for example, a CMOS PAL device of type PLC18V8Z35 marketed by Philips Semiconductor Corp of Sunnyvale, Calif. Timer/Shutdown logic 70 represents the logic component of a control assembly represented generally at 76. In this regard, the logic component 70 responds to user input or user controls as represented at block 78 and line 80. Such control inputs from the user control 78 will include a start actuation function to derive a start input, as well as a stop actuation to derive a stop input. The logic function 70 additionally responds to clinician control inputs as represented at block 82 and line 84. These clinician controls 82 are concealed such that the device can be used by the patient. However, such control inputs which are not accessible by the patient will include the total dosage permitted in terms of the times and duration of application of the therapy, as well as the parameters of the waveform and frequency. Accordingly, the user controls at 78 are primarily an on and an off function to commence or terminate a given therapy.

Upon the voltage converters reaching their designated or target (threshold) voltage and current levels, the logic function 70 will provide a timing output representing the time interval remaining in a given therapy session. This visual indicia is represented at line 86 and block 88. Additionally, the logic function 70 will provide an output representing an appropriate on-going therapeutic interval which may be provided, for example as a green light emitting diode (LED). Additionally, where any electrode as at 20, 24 and 26 exhibits an anomaly such as being improperly positioned, a warning indicia will be provided and, further, where a monitored condition is derived which calls for a stopping of a therapy, a red LED will be illuminated in conjunction with a system shutdown. This status display output from the logic function 70 is represented at line 90 and block 92.

Returning to the voltage converter functions, the higher frequency, f1, waveform 10 as well as the lower frequency, f2, burst frequency and output timing intervals are generated in rectangular wave fashion utilizing one half H bridge drivers. In this regard, the first channel (A) d.c. positive voltage output at line 52 and the negative d.c. voltage output at 53 are seen directed to a bridge driver represented at block 94. In similar fashion, the corresponding second channel (B) voltage converter outputs at lines 54 and 55 are directed to the inputs of an identical bridge driver represented at block 96. Drivers 94 and 96 may be provided as incorporating half-bridge N-channel power MOSFET drivers, for example, a type LT1160 marketed by Linear Technology Corporation of Milpitas, Calif. These devices 94 and 96 are under the common control of a waveform generator represented at block 98. Such control is represented at lines 100 and 102. In turn, the waveform generator 98 is under the control of the logic function 70 as represented at line 104. The generator function 98 may be implemented, for example, as a CMOS timer of type LMC555 marketed by National Semiconductor Corporation (supra).

It is from the waveform generator function 98 that the rectangular wave discussed in connection with FIGS. 1 and 2 is developed by control over the positive and negative inputs to the bridge drivers 94 and 96. At the commencement of a given therapy, the peak—to—peak value of this waveshape as now developed respectively at lines 106 and 108 from drivers 94 and 96, will progressively increase in value until such time as a peak target (threshold) current is reached. At that time, the waveshape is under stabilization control in terms of current and voltage for the duration of the therapeutic treatment. A current sensing function for the channel "A" output at line 110 is represented at block 112. Operating in conventional manner, the sensor function 112 produces a voltage signal at line 114 having a value which is proportionate to the instantaneous value of current at line 110. Sensor 112 may be implemented with a type PE63587 current sense transformer marketed by Pulse Corp of San Diego, Calif. The signal at line 114 is shown, inter alia, being directed via line 116 to a peak current detector represented at block 118. Detector 118 may be implemented, for example, with a high speed, BiFET operational amplifier marketed as a type AD711 by Analog Devices, Inc., (supra). As the ramp threshold is reached, an output from the peak current detector 118 at line 120 functions to stabilize the ramp generator 58 for this one channel, A.

The second channel, identified as output B, as derived in conjunction with bridge driver 96 and line 108, incorporates an identical current sensor represented at block 122 and the excitation output is seen to continue as represented at line 124. Current sensor function 122 provides a signal, corresponding with the current at line 124, along lines 126 and 128 to a peak current detector function represented at block 130. A signal output from peak current detector 130 is directed, as before, via lines 132 and 134 to the ramp generator 60, functioning to cause a stabilization of that ramp output upon reaching the value of a ramp threshold signal or value.

Peak voltage detection is carried out for the first channel identified as output A by a peak voltage detector function represented at block 136. In this regard, voltage is monitored from output line 110 as represented at lines 138 and 140 and, as before, the voltage detector function may be implemented with a high speed, BiFET operational amplifier of a type AD711 (supra).

The peak voltage detection function is repeated in conjunction with the second channel represented as output B. In this regard, the peak voltage detection function is represented at block 142 for this second channel. Voltage monitoring is from output line 124, which is seen connected with lines 144 and 146 leading to the detection function 142. The output of peak voltage detector 142 is seen at line 148 to be extending to one input of a Range Comparators function represented at block 150. In this regard, the peak current detector output at line 132, which also extends to comparators function 150, provides a monitored current value output. Correspondingly, the peak voltage detector provides a monitored voltage value output. These outputs are specific to the second channel represented as output B. The comparators function 150 may be implemented, for example, with high-speed comparators such as type LM119 marketed by National Semiconductor Corporation (supra). Both during the ramping procedure and following that procedure during therapy, when the monitored current value output at line 132 and the monitored voltage output at line 148 represents a load impedance not within a predetermined load impedance range, then an impedance fault signal specific to the second channel represented at output B will be generated by the comparators 150 and presented to the timer shutdown logic 70 as represented at line 152. The control assembly 76 then will respond to such an input to derive a stop input terminating the generation of excitation outputs at lines 110 and 124.

In similar fashion, the monitored current value output from peak current detector 118 at line 154 and the corresponding monitored voltage value output from peak voltage detector 136 at line 156 are directed to a Range Comparators function represented at block 158. The comparators function 158 responds to a predetermined load impedance value and derives an impedance fault signal for the first channel represented as output A when the monitored voltage value output and the monitored current value output at respective lines 156 and 154 represent an impedance not within the predetermined load impedance range. A first channel designated impedance fault signal then is created at line 160 which is directed to the timer/shutdown logic at block 70 to turn off the apparatus. At such time that the currents are turned off, an appropriate fault indicia is provided at the status display 92.

Figure 4A:
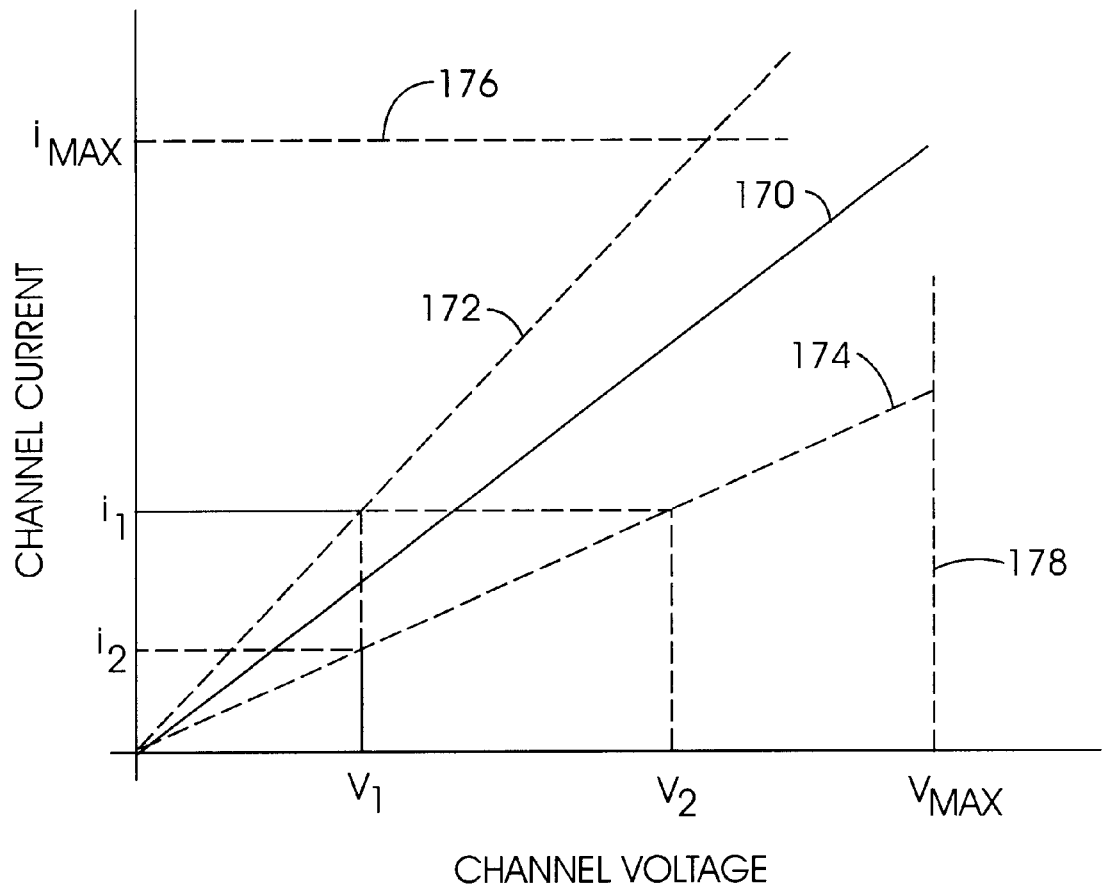
FIG. 4A is a graphical representation of threshold ranges utilized by the circuit of FIG. 4 for determining impedance characteristics for each channel.

An interesting aspect of the fault evaluation made by the range comparators resides in the impedance based nature of the fault. For example, the predetermined load impedance range or acceptable load impedance range which is employed by the range generators 150 and 158 may be represented by a sequence of acceptable voltages and acceptable currents extending between zero value at the commencement of ramp generation to maximum values which will be realized when the ramp threshold signal is generated stabilizing the outputs of the two drivers 94 and 96. These voltage and current impedance characteristics can be graphically portrayed. Looking momentarily to FIG. 4A, for a given channel, channel current is plotted in relationship to channel voltage, a target or median relationship being represented by the solid line 170. A first or upper acceptable increasing range of voltage and corresponding current values is represented by the dashed line 172. Correspondingly, a second range of increasing acceptable voltage and corresponding current values is represented as a second lower range at dashed line 174. The ramp threshold values are represented as $i_{max}$ at dashed line 176, while the corresponding threshold value for voltage is represented as $V_{max}$ at dashed line 178. Because of the impedance characteristic at the feed electrodes fastened to the skin region of the patient, for a given value of voltage, for example, that shown at $V_1$, an acceptable highest value of current is represented at $i_1$. However, for that voltage value, $V_1$, if the current is less than the corresponding acceptable value current of the second or lower range 174, i.e., below $i_2$, then an impedance fault signal is derived as an electrode fault signal indicating to the practitioner that an electrode for the channel at hand is not properly installed. By contrast, the control assembly derives the impedance fault signal as a low impedance fault signal, e.g., resembling a short circuit, when for any given value of voltage of both the first and second ranges at dashed lines 172 and 174, the value of current is greater than the corresponding acceptable value of the current of the higher or first range represented at dashed line 172. For example, if the current falls between locations $V_1$ and $V_2$, a current higher than $i_1$ will evolve an impedance fault signal. These two types of impedance fault signals are indicated to the practitioner at the status display 92.

Returning to FIG. 4, the apparatus of the invention additionally carries out a test for waveform balance between the output at line 110 and the output at line 124. This inter-channel output test feature is represented at block 180 which, for the instant embodiment, compares the amplitudes of current of the first channel represented as output A and the second channel represented as output B. In this regard, note that the current sensor 112 output is directed via line 114 and line 182 to one input of the waveform balance network 180. The same form of input from current sensor 122 is directed via lines 126 and 184 to the opposite input to the network 180. While any of a variety of waveform characteristics may be employed for this inter-channel waveform balance evaluation, that shown is one wherein a peak value of current at one channel is monitored and compared with a corresponding peak value of current in the second channel. The peak current difference value then is compared to a predetermined peak current balance limit value. A balance fault signal is generated at line 186 when the peak current balance value exceeds the predetermined peak current balance limit value. That signal, in turn, causes the Timer/Shutdown logic 70 to terminate the outputs of the two channels and provide a corresponding fault massage at the status display 92.

As indicated earlier herein, the high frequency components of the waveform will exhibit positive and negative energy equivalence in order to avoid any presence of a net d.c. waveform term. Avoidance of such a term prevents salt buildup in tissue, an undesirable condition referred to as "iontophoresis". Accordingly, the monitoring functions for the apparatus include a d.c. off-set Integrator/Detector for each of the channels identified as having output A and output B. Concerning the former, it may be observed that the signal from current sensor 112 is monitored via lines 114 and 188 by an Integrator/Detector represented at block 190. Accordingly, should the detector 190 identify a d.c. offset, a fault signal is transmitted to the Timer/Shutdown logic 70 to turn off current in both channels as represented by arrow 192.

The second channel, identified as output B similarly is monitored for a d.c. offset. In this regard, a signal from current sensor 122 is presented along lines 126 and 192 to a d.c. offset Integrator/Detector represented at block 194. Upon detecting any d.c. offset, detector 194 similarly provides a fault signal to the Timer/Shutdown logic 70 as represented by arrow 196. As before, this causes the apparatus to be turned off. When any such d.c. offset fault signal occurs, an appropriate message is provided at the status display 92

In the interest of patient safety, both of the channels of the apparatus are monitored by an over-current detector as represented at block 200 and an over-voltage detector represented at block 202. In this regard, over-current detector 200 responds to the current value signal from current sensor 112 as represented at line 114, as well as to the corresponding signal from current sensor 122 as represented at line 126. This overcurrent detector may be implemented, for example, as a high-speed comparator of a type LM119 marketed by National Semiconductor Corp. (supra). This over-current detector is "hard wired" such that its response is both immediate and reliable in providing a fault signal at line 204 leading to the Timer/Shutdown logic 70 which carries out a shutdown procedure and appropriate indication at display 92. Over-voltage detector 202 responds to voltage values at line 110 as represented at line 138 and corresponding voltage values at line 124, as represented at line 144. Where that detector 202 determines that the monitored voltage at either line 138 or line 144 is above a predetermined limit, then a corresponding fault signal is directed via line 206 to the Timer/Shutdown logic 70. The apparatus, as before, is shutdown and an appropriate message is provided at the display 92. Over-voltage detector 202 similarly is "hard wired" in the interest of precision and speed and may be provided as a type LM119 comparator as described above.

As indicated earlier herein in connection with FIG. 1, an aspect of the present invention is a recognition that a squarewave with positive-going and negative-going waveform components and which exhibits substantially no d.c. term is derived which occurs at a base frequency value (F1) and at a burst repetition frequency value (F2) less than that base frequency value. The electrical characteristics of tissue with which the electrodes are associated may be analyzed in conjunction with the applied waveform for diagnostic purposes as well as being used for therapeutic purposes. For diagnosis, the voltage data and current data obtained by monitoring can be treated mathematically in a variety of foreseeable approaches. For example, Fourier transforms of the parameters of voltage and current can provide analysis. Additionally, the Laplace equation can be solved in various ways to compute admittance as a function of space within a tissue sample by applying a changing voltage at various points across the sample. This is referred to as electrical impedance tomography. The following Laplace equation relates these:

$$\nabla \cdot \sigma \nabla \phi = 0 \qquad (1)$$

The del or $\nabla$ operation is merely a shorthand way to write the sum of three partial differentials of an unknown function distributed through space, $\phi$ being potential and $\sigma$ being admittance. The form varies with the coordinate system used. For a Cartesian coordinate system and a real function, R, (without complex i components) the following expression obtains:

$$\nabla R = \partial R/\partial x + \partial R/\partial y + \partial R/\partial z \qquad (2)$$

A partial differential like $\partial R/\partial x$ represents a change in R along the x direction. The del of R is the simultaneous change in all directions at once. The resulting function is a collection of values spread across space. This is also is called the gradient of R.

Figure 5A:
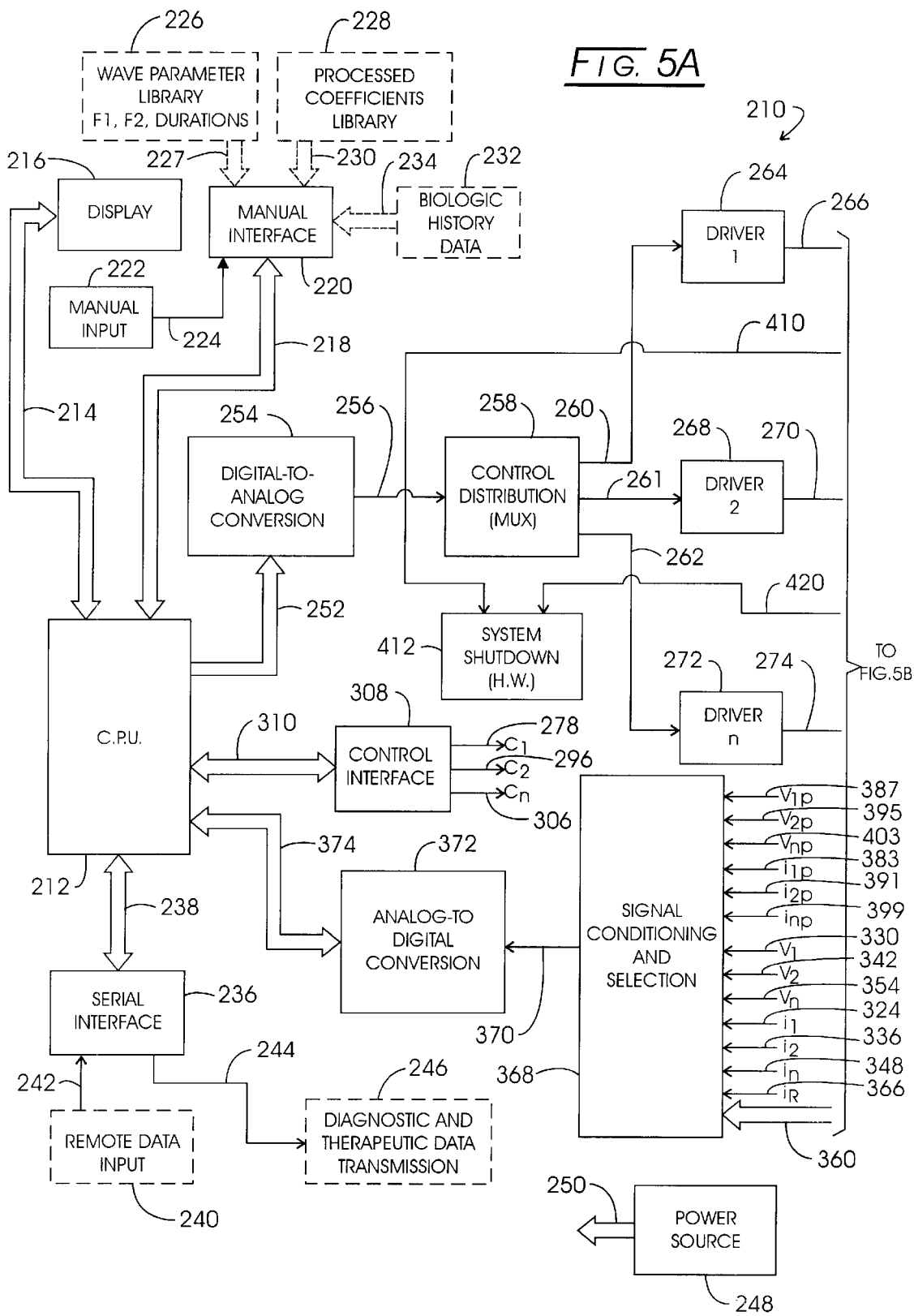
FIGS. 5A and 5B combine as labeled thereon to show a block schematic systems diagrams for another embodiment of the invention.
Figure 5B:
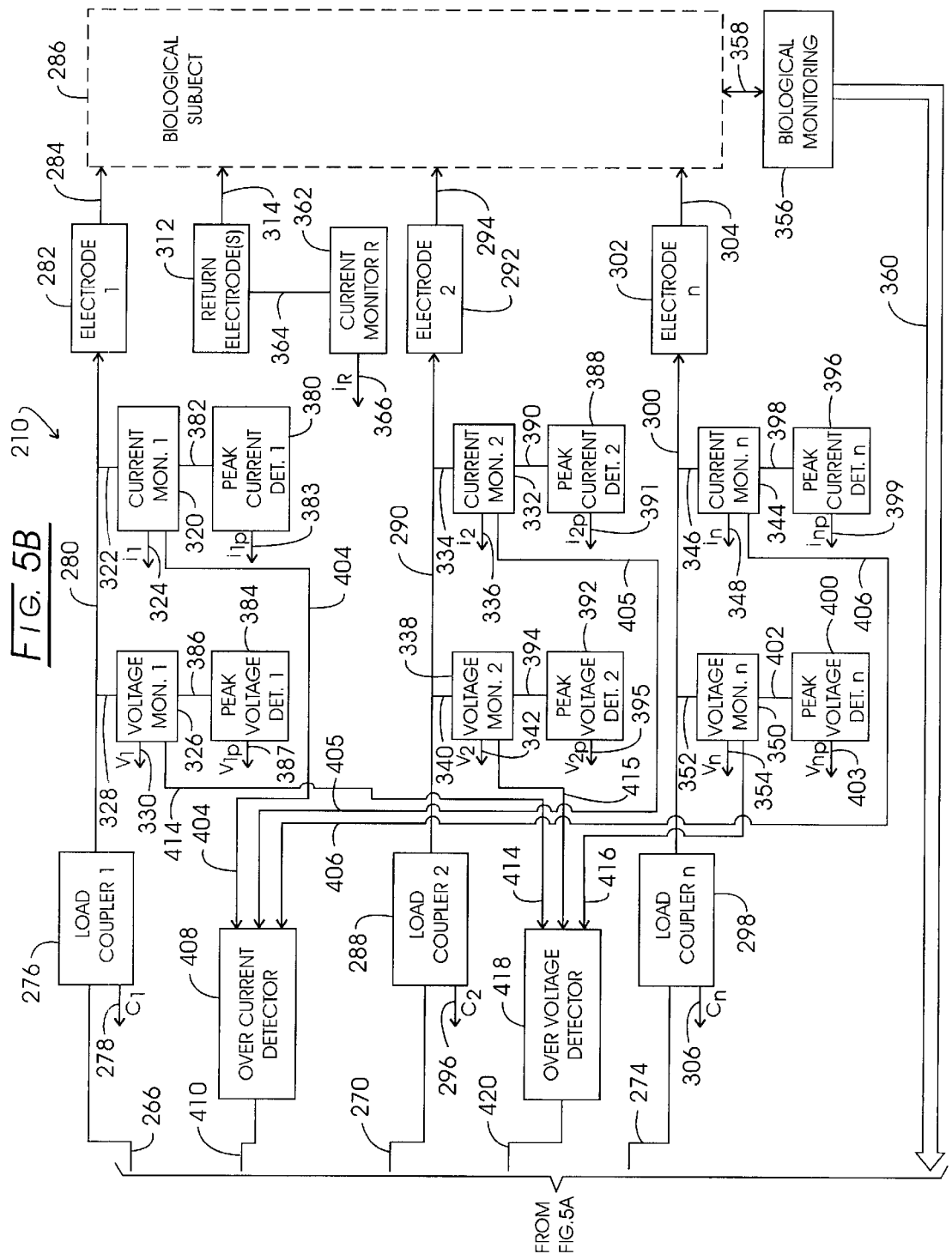

A system for permitting diagnostic analysis as well as for subsequent therapy is represented in FIGS. 5A and 5B which should be combined as labeled thereon. The system represented in FIGS. 5A and 5B is one performing in conjunction with a controller or central processing unit (C.P.U.) with memory, various interfaces and display. Represented generally at 210, this system is seen to perform in conjunction with a controller (C.P.U.) 212. Controller 212 interacts, as represented by bus 214, with a display represented at block 216. Similarly, the controller 212 interacts with a manual interface as represented at bus 218 and block 220. Interface 220 may be the receptor of a variety of inputs such as the manual input or keyboard type function represented at block 222 and line 224. Also insertable through the manual interface 220 may be any of a broad variety of waveform types and parameters including the above-noted F1 and F2 waveform frequencies and related data as represented by the dashed block 226 and dashed arrow 228. Where that waveform data has been mathematically processed to develop corresponding coefficients and the like, then such library of processed coefficients can be introduced at the manual interface 220 as represented at dashed block 228 and dashed arrow 230. Similarly, biologic history, either derived from the patient under investigation or pools of patients, can be introduced at the manual interface 220 as represented at dashed block 232 and dashed arrow 234. In conventional fashion, interactive remote data can be provided at the controller 212 as represented at a serial interface 236 and interactive bus 238. The inputting of remote data to the interface 236 is represented at dashed block 240 and line 242. Correspondingly, serial data can be outputted which, for example, will relate to diagnostic and therapeutic information as represented at line 244 and dashed block 246. Power to the components of the system 210 is represented at block 248 and arrow 250.

System 210 may perform in conjunction with one or more channels and an associated return electrode function. In order to customize waveform parameters or waveshapes (see FIG. 2), the controller 212 supplies digital information to a digital-to-analog converter function as represented at bus 252 and block 254. The resulting analog output at line 256 is directed to a distribution function similar to a multiplexer as represented at block 258. Block 258, in turn, distributes the analog waveforms to a select number of channels. In this regard, n (three or more) channels are shown in the instant representation by each responding to an analog input directed from the distribution function 258 to channel input lines 260–262. Line 260 is seen directed to the input of a channel number one driver at block 264, the output of which is provided at line 266. Line 261 is directed to the input of a driver for channel two as represented at block 268, the output of driver 268 being at line 270. Line 262 extends to the nth driver as represented at block 272. This nth channel driver provides an output at line 274.

Looking additionally to FIG. 5B, line 266 is seen to extend to a first channel load coupler represented at block 276. Coupler 276 functions, for example, to handle varying impedances of an associated electrode with the biological subject being diagnosed or investigated as well as treated. This impedance-based function may be automated ultimately from the controller 212, as initially represented by the control input arrow 278 labeled "$C_1$". The output of coupler 276 at line 280 provides a selected waveform to a first channel electrode represented at block 282. This electrode 282 for channel one is shown electrically associated, as represented at arrow 284, with a biological subject represented at the dashed boundary 286.

The second channel output at line 270 is seen directed to a second channel load coupler represented at block 288 having an output represented at arrow 290 extending to the second channel electrode represented at block 292. The signal coupling of electrode 292 with the biological subject 286 is represented by an arrow 294. Load coupler 288 also is controllable, for example, to carry out automated impedance handling by control inputs shown at arrow 296 and labeled "$C_2$". The nth channel driver output at line 274 is shown directed to a channel n load coupler represented at block 298 having an output represented by arrow 300. Arrow 300 is seen directed to the nth electrode represented at block 302. The electrical association with the electrode 302 and the biological subject 286 is represented at arrow 304. Control over a load coupler n at 298 is provided, for example, for purposes of automated impedance handling as represented at arrow 306 which is labeled "$C_n$".

Returning to FIG. 5A, this load coupler control as represented at lines 278, 296 and 306 is carried out by the controller 212 operating in conjunction with a control interface as represented at block 308. Interactive control to the interface 308 is represented at bus 310 and the arrows 278, 296 and 306 reappear in conjunction with the noted labels: $C_1$, $C_2$, and $C_n$.

Returning to FIG. 5B, one or more return electrodes is provided with the system 210 as represented at block 312.

The electrical association between the return electrode function 312 and the biological subject 286 is represented at arrow 314.

System 210 provides for the monitoring of both electrical and biological parameters in order to acquire sufficient data for mathematical processing or treatment and additionally to develop safety features. Accordingly, the excitation outputs at lines 280, 290 and 300 are monitored in addition to a monitoring of the current extant at the return electrode 312. A current monitor represented at block 320 and line 322, monitors current values at line 280. An RMS value of monitored current, $i_1$ is represented at arrow 324. Similarly, the voltage levels at line 280 are monitored, as represented at block 326 and line 328, to provide a monitored RMS voltage output labeled, $V_1$ at arrow 330. These RMS current and RMS voltage values permit the system 210 to carry out a signal power monitoring function. The excitation outputs at line 290 is monitored for current values as represented at block 332 and line 334. An RMS value of monitored current for this second channel is labeled $i_2$ at arrow 336. An RMS voltage level at excitation output line 290 is monitored, as represented at block 338 and line 340, to provide a monitored voltage output labeled $V_2$ at arrow 342. Current monitoring of the excitation output at line 300 is provided for the nth channel as represented at block 344 and line 346. This develops an nth channel monitored RMS current signal labeled $i_n$ at arrow 348. Similarly, voltage at line 300 is monitored as represented at bock 350 and line 352 to provide a monitored RMS voltage output labeled $V_n$ at arrow 354.

Biological monitoring of the subject 286 is represented at block 356 and dual arrow 358. The type of monitoring data is elected by the attending physician and will include, for example, respiratory rates, blood oxygen, heart rate, temperature, brain wave data and the like. The resultant data stream is represented at bus 360. Monitoring function 356 also may be utilized in conjunction with select biological parameters for homeostasis in conjunction with determined biological limits for such biological parameters. With this arrangement, trends can be monitored and warnings supplied from the controller 212 in the event of adverse reactions during diagnosis or treatment. Finally, current extant at the return electrode 312 is monitored as represented by block 362 and line 364. This monitor provides a return current signal labeled $i_R$ at arrow 366.

In general, the thus monitored data will be analog in nature and is introduced to the controller 212 following its conversion to digital format. In this regard, returning to FIG. 5A, the analog monitored RMS voltage signals $V_1$, $V_2$ and $V_n$ reappear in conjunction with respective arrows 330, 342 and 354. Similarly, the monitored RMS current values $i_1$, $i_2$, $i_n$ and $i_R$ reappear with respective arrows 324, 336, 348 and 366. Finally, bus arrow 360, carrying biological data, reappears. All of these signals are shown being introduced to a signal conditioning and selection function 368 which selectively conveys them, as represented at line 370, to an analog-to-digital converter represented at block 372. Converter 372 samples the data at line 370 and provides a corresponding digital data input to controller 212 as represented at bus 374.

As in the earlier embodiment, system 210 employs "hard wired" overcurrent and overvoltage detection components. In this regard, for the first channel, the monitored current value output, represented at block 320, is provided at line 404. In similar fashion, the monitored voltage value output for the first channel, as represented at block 326, is provided at line 414. For the second channel, the monitored current value output of block 332 is provided to line 405. The monitored voltage value output as derived at block 338 is provided at line 415 for the second channel. Finally, the monitored current value output deriving at block 344 for the nth channel is provided at line 406. The corresponding voltage value output derived at block 350 is provided at line 416.

Monitoring signal carrying lines 404, 405 and 406 representing instantaneous current values and corresponding respectively with the first, second and nth channels to an overcurrent detector represented at block 408. Upon detection of an overcurrent, as represented at line 410 and block 412 seen in FIG. 5A, the hard wired system shutdown feature is implemented to turn off current to all electrodes. In similar fashion monitoring signal carrying lines 414, 415 and 416, representing instantaneous voltage values and corresponding respectively with the first, second and nth channels are directed to a hard wired overvoltage detector represented at block 418. Upon the occurrence of an overvoltage condition, as represented at line 420 and block 412, a hard wired overvoltage system shutdown ensues in the manner similar to that occurring with overcurrent conditions.

Peal-to-peak voltage and current values also are useful for computer-based analytic purposes. Accordingly, peak current at excitation line 280 is monitored as represented at block 380 and line 382. The resultant first channel monitored peak current signal, which may be the peak current of a given cycle or an average peak current measured over a number of cycles, is represented at arrow 383 labeled, $i_{1p}$. Peak current is monitored at excitation line 290 for the second channel as represented at block 388 and line 390. The resultant second channel monitored peak current signal is represented at arrow 391 labeled, $i_{2p}$. This peak current signal also may be representative of a single cycle or an average value determined over multiple cycles. Lastly, peak current at excitation line 300 is monitored as represented at block 396 and line 398. The resultant $n^{th}$ channel monitored peak current signal is represented at arrow 399 labeled $i_{np}$. As with the previous two peak current values, the peak current represented at arrow 399 represents either the peak current of a given cycle or an average of the peak current values for multiple cycles.

Peak voltage at excitation line 280 is monitored as represented at block 384 and line 386. The resultant first channel monitored peak voltage signal is represented at arrow 387 labeled, $v_{1p}$. Peak voltage is monitored at excitation line 290 for the second channel as represented at block 392 and line 394. The resultant second channel monitored peak voltage signal is represented at arrow 395, labeled, $v_{2p}$. Finally, peak voltage at excitation line 300 is monitored as represented at block 400 and line 402. The resultant nth channel monitored peak voltage signal is represented at arrow 403, labeled $v_{np}$.

Returning to FIG. 5A, the analog peak monitoring signals are seen to be directed to the signal conditioning and selection function 368. In this regard labeled peak current arrows 383, 391 and 399 as well as labeled peak voltage arrows 387, 395 and 403 reappear as being directed to block 368. The latter signal conditioning and selection function selectively conveys them, as represented at line 370 to analog-to-digital converter represented at block 372. Converter 372 samples the data at line 370 and provides corresponding digital data to controller 212 as represented at bus 374.

An advantage of utilizing a controller-based system 210 resides in the substantial flexibility afforded the user in carrying out not only therapy, but diagnosis utilizing variations of excitation inputs and taking advantage of available memory for recording numerical data corresponding with measured patient electrical characteristics both with respect to individual patients and with respect to patient pools. FIGS. 6A–6G combine to set forth a flowchart of one such program under which the controller 212 may operate.

Figure 6A:
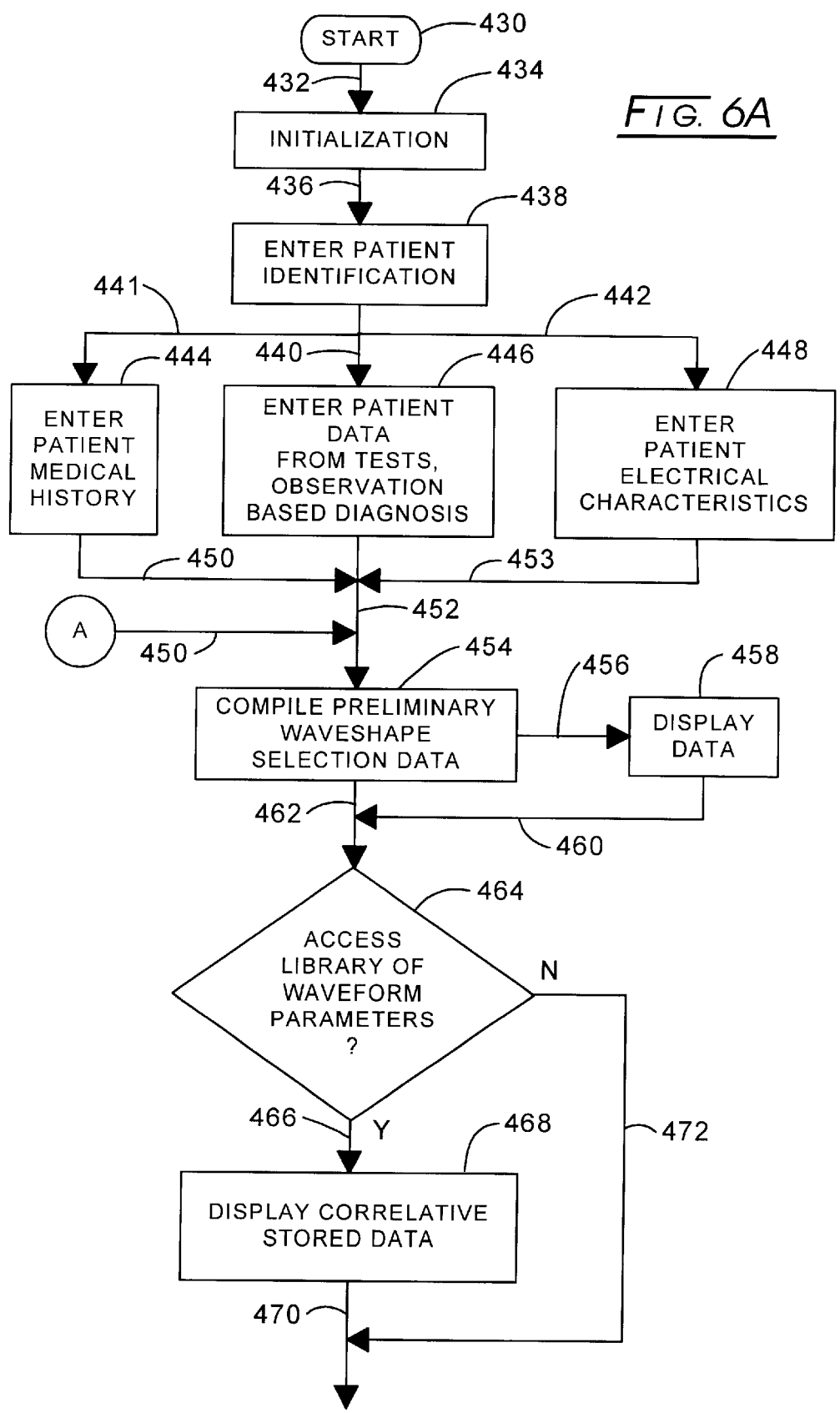

Looking to FIG. 6A, the program is seen to commence at start node 430 and, as represented at line 432 and block 434, a conventional initialization procedure then is carried out. The program then continues, as represented at line 436 and block 438, to provide for the entry of the identification of the patient. At this point, the practitioner is afforded the opportunity of entering any preexisting patient data into memory for purpose of establishing records and generally enhancing the data base for the patient. Thus, the program continues as shown at lines 440–442 to provide for the entry of patient medical history, as represented at block 444; the entry of patient data from test observation and any observation-based diagnosis, as represented at block 446; and the entry of measured patient electrical characteristics which might be available, as represented at block 448. The program then continues as represented at lines 450–452 to the instructions at block 454 which provide for the compiling of preliminary waveshape selection data. That compilation is then displayed as represented at line 456 and block 458. The program then continues, as represented at lines 460 and 462, to the query posed at block 464. Block 464 affords the practitioner an opportunity to determine whether or not to access a library of waveform parameters. Such parameters have been discussed, for example, in conjunction with FIG. 5A at blocks 226 and 228. In the event such access is desired, then the program continues as represented at line 466 and block 468 providing for a display of such correlative stored data. The program then continues as represented at line 470. In the event of negative determination with respect to the query posed at block 464, then the program continues as represented at line 472 to line 470.

Figure 6B:
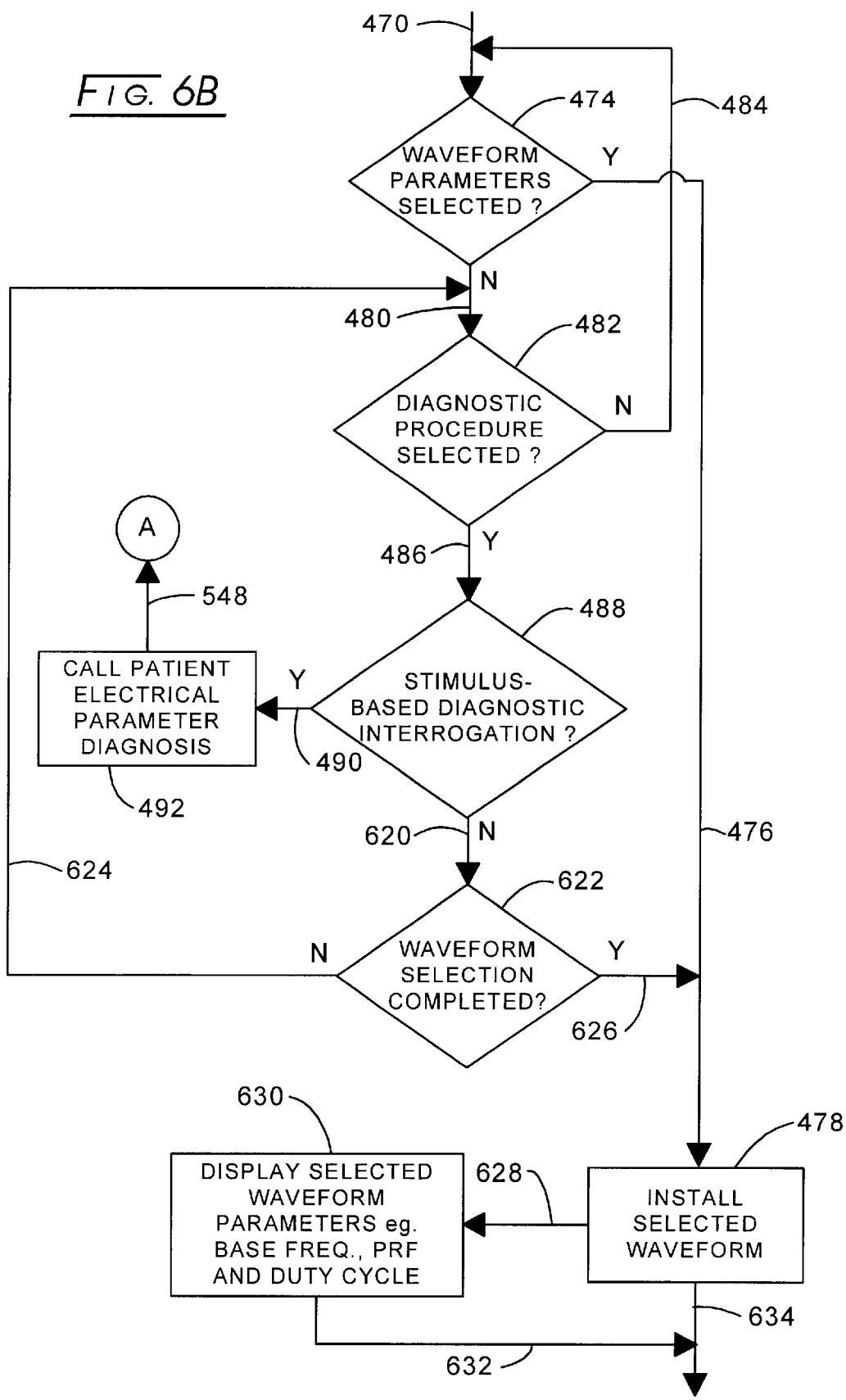

Line 470 reappears in FIG. 6B extending to the query posed at block 474 determining whether the practitioner has at this point in time selected the waveform parameters desired. In the event that such waveform parameters (waveshape) have been selected, then the program proceeds to install that selected waveform as represented at line 476 and block 478.

Where the waveshape has not been selected at this juncture in the program, then as represented at line 480 and block 482 a determination is made as to whether the practitioner wishes to carry out a diagnostic procedure for purposes of determining an appropriate waveshape. In the event of a negative determination, then the program reverts to line 470 and the query at block 474 as represented by line 484. Where a diagnostic procedure is elected, then as represented at line 486 and block query 488, a determination is made as to whether a stimulus-based diagnostic interrogation is desired. In the event that such interrogation is called for, then, as represented at line 490 and block 492 a patient electrical parameter diagnosis is called.

Figure 7:
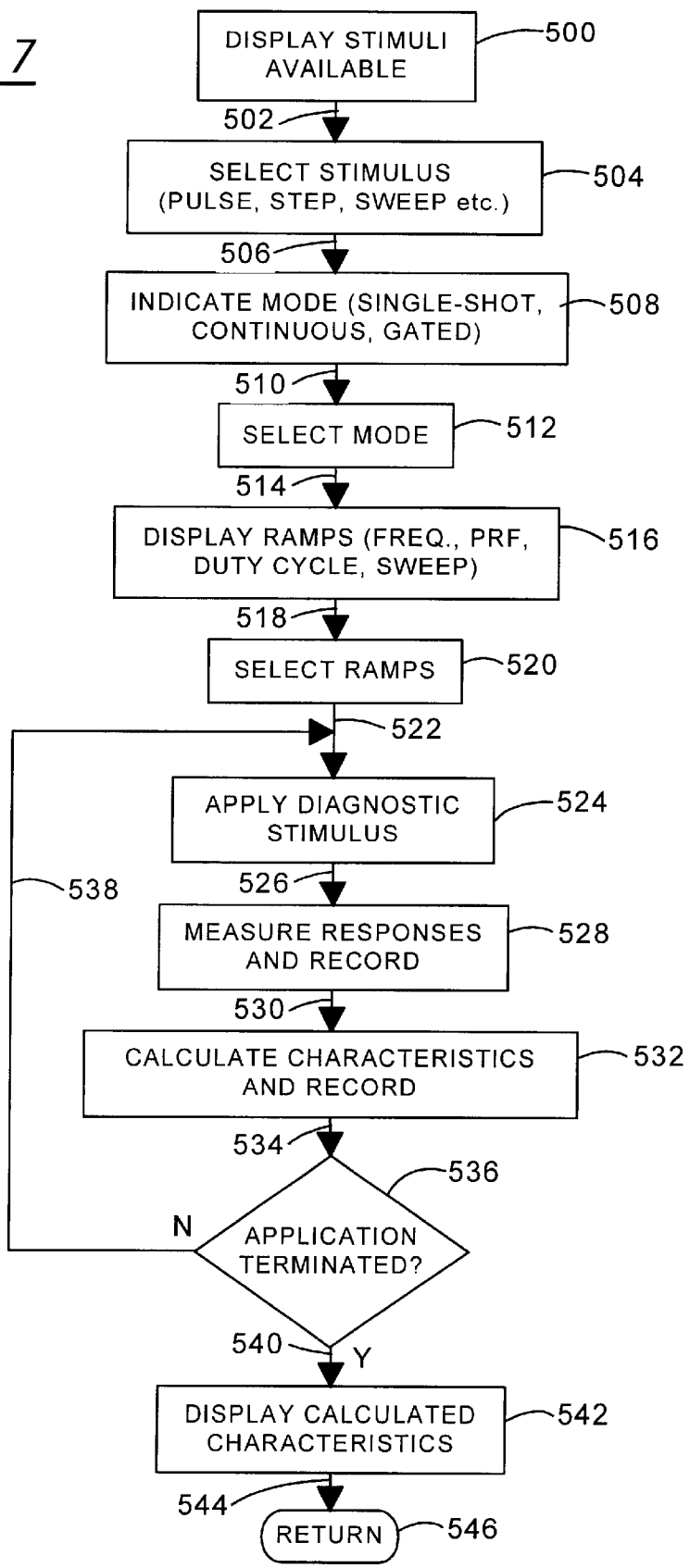
FIGS. 7 is a flowchart describing a general diagnostic procedure for the system of FIGS. 5A and 5B.

Referring to FIG. 7, a generalized version of this subroutine is depicted in flowchart fashion. The routine commences at block 500 providing for a display of the stimuli which are available with the system for selection by a practitioner. Then the routine continues as represented at line 502 and block 504 wherein the practitioner selects a particular stimulus, for example, whether it be of a pulse variety, a step variety or a frequency sweep variety. As represented at line 506 and block 508 the mode of the selected stimulus is selected. This mode may be a single shot impulse, a continuous excitation or a gated excitation. Then, as represented at line 510 and block 512, the practitioner selects one of the thus displayed modes and the program continues as represented at line 514 and block 516. The system provides a prompt for selecting ranges with respect to such parameters as frequency, pulse repetition frequency, duty cycle and sweep range. Where a sweep frequency diagnosis is desired, then, as represented at line 518 and block 520, that range data is selected and, as represented at line 522 and block 524, a diagnostic stimulus is applied to the patient and, as represented at line 526 and block 528, responses are measured and recorded. Such a response, for example, may be current waveshape at the feedpoint of the electrodes. Then, as represented at line 530 and block 532, certain characteristics of the measured responses are calculated and recorded. Such characteristics will, for example, be a quotient form of treatment of the Fourier transforms of the applied voltage squarewave and of the current waveform at feedpoint of the electrodes. Additionally, Laplace based analysis may be carried out. Next, as represented at line 534 and block 536 a query is made as to whether the application has terminated. In the event that it has not, then the program loops, as represented at line 538, and continues the application of stimulus. In the event the application of stimulus is terminated, then as represented at line 540 and block 542, the calculated characteristics are displayed and, as represented at line 544 and node 546 the routine returns.

Figure 8:
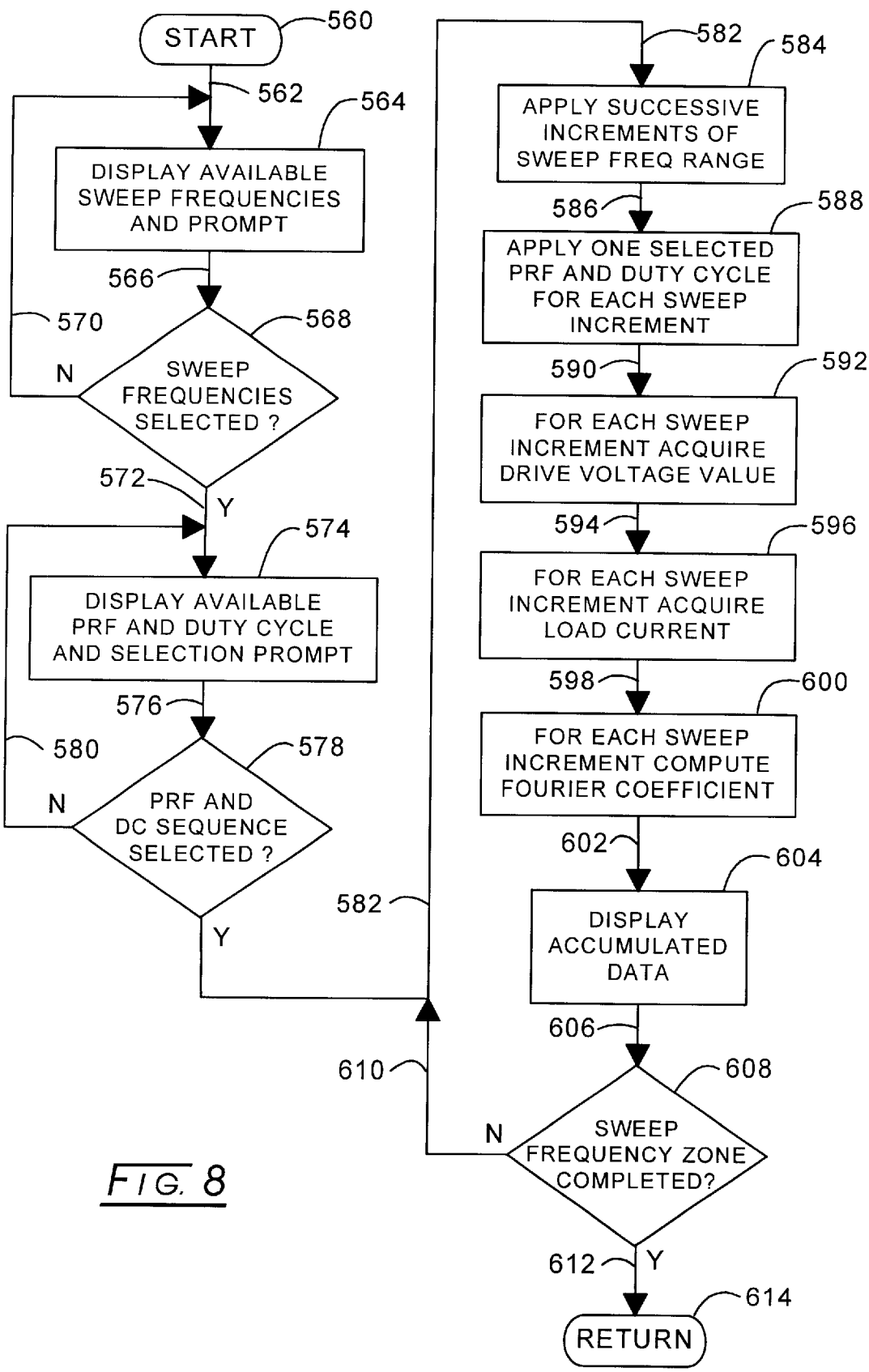
FIG. 8 is a block diagrammatic representation for a sweep frequency form of diagnostic procedure utilized by the system of FIGS. 5A and 5B.

Returning to FIG. 6B and block 492, upon the return of the subroutine, as represented at line 548, the program reverts to node A which reappears at FIG. 6A at line 450 extending to line 452.

Where the system is more dedicated in that it provides diagnostic activity based upon sweep frequencies then a routine described in connection with FIG. 8 may be called. Looking to that figure, the routine commences at node 560 and line 562 leading to block 564. Block 564 provides for the display of available sweep frequencies along with appropriate prompts to aid the practitioner in their selection. Then, as represented at line 566 and block 568 a query is made as to whether a zone or range of sweep frequencies has been selected. In the event that it has not, then as represented at line 570, the program loops until such time as a selection has been made. Upon making the sweep frequency selection, then as represented at line 572 and block 574 the routine displays available repetition frequencies and duty cycles along with an appropriate selection prompt. Then, as represented at line 576 and block 578 a query is made as to whether the selections made available at block 574 have been made. In the event they have not, then, as represented at line 580, the routine loops until such selection is made. Where a selection has been made, then, as represented at line 582 and block 584 successive increments of the sweep frequency range are applied to the system electrodes and, as represented at line 586 and block 588 one selected pulse repetition frequency and duty cycle is applied for each sweep increment. The routine then continues as represented at line 590 and block 592 wherein, for each sweep increment, the routine acquires the drive voltage value and, as represented at line 594 and block 596, for each sweep increment, the routine acquires the load current or current at the electrode feed point. Then, as represented at line 598 and block 600, for the instant application, for each sweep increment a Fourier coefficient with respect to both voltage and current is computed. As noted above, other mathematical processing involving Laplace equations and the like can be carried out. Then, as represented at line 602 and block 604, accumulated data is displayed from which the practitioner may form a diagnosis. The routine continues as represented at line 606 and block 608 so as to determine whether or not the sweep frequency zone has been completed. In the event that is has not, then the program loops as represented at lines 610 and 582 until the frequency sweep has been conducted throughout the elected zone. Where that sweep zone has been completed, then as represented at line 612 and node 614, the routine returns and the program reverts to the earlier described node A.

Returning to FIG. 6B, where the query posed at block 488 results in a negative determination, then as represented at line 620 and block 622, a determination is made as to whether the waveform selection has been completed. In the event that it has not, then the program loops as represented at line 624. However, where waveform selection is completed, then as represented at lines 626 and 476, the waveform is installed as earlier described in connection with block 478. As represented at line 628 and block 630 the selected waveform parameters are displayed. Those parameters will, for example, be the base or higher frequency, the pulse repetition frequency and duty cycle. With such display, the program continues as represented at lines 632 and 634.

Line 634 reappears in FIG. 6C. Looking to that figure, the line is seen to be directed to block 636 providing for the loading of treatment intervals. Those intervals will be the total treatment time which will be a time, for example, representing the maximum allowable time of treatment accumulated over a lengthy interval such as a month or year. Next, the dosage interval is loaded. The dosage interval is the interval of a given treatment and the accumulation of dosage intervals cannot exceed the total treatment time. As represented at line 638 and block 640, both the elected treatment (DOSAGE, ACCUMULATED) intervals are displayed and the program continues as represented at line 642 and block 644 wherein the power source status is acquired. For example, if the power source is a battery, then it is important to know that the battery has sufficient capacity to power the system for the dosage interval at hand. Accordingly, as represented at line 646 and block 648 an inquiry is made as to whether the power source is ok. In the event that it is not, then as represented at line 650 and block 652 the resultant error is displayed to the practitioner and, as represented at line 654 and block 656, the procedure is stopped and the program reverts to line 634 as represented at line 658.

If the power source is determined to be adequate, then as represented at line 660 and block 662, prompts are displayed for the entry of electrical parameter limits and ramp rate. The program then continues as represented at line 664 and block 666 wherein the ramp rate is installed. Next, as represented at line 668 and block 670, the ramp current and voltage specifications are entered. Following such installation, as represented at lines 672 and block 674 acceptable ramp current and slope ranges are installed. This data has been discussed above in connection with FIG. 4A. The program continues as represented at line 676 and block 678 wherein the balance window of acceptance between channels is entered, or a preprogrammed default interval is accepted. Next, as represented at line 680 and block 682 prompts are displayed for using or applying physiological monitors as have been discussed above. The program then continues as represented at line 684.

Figure 6D:
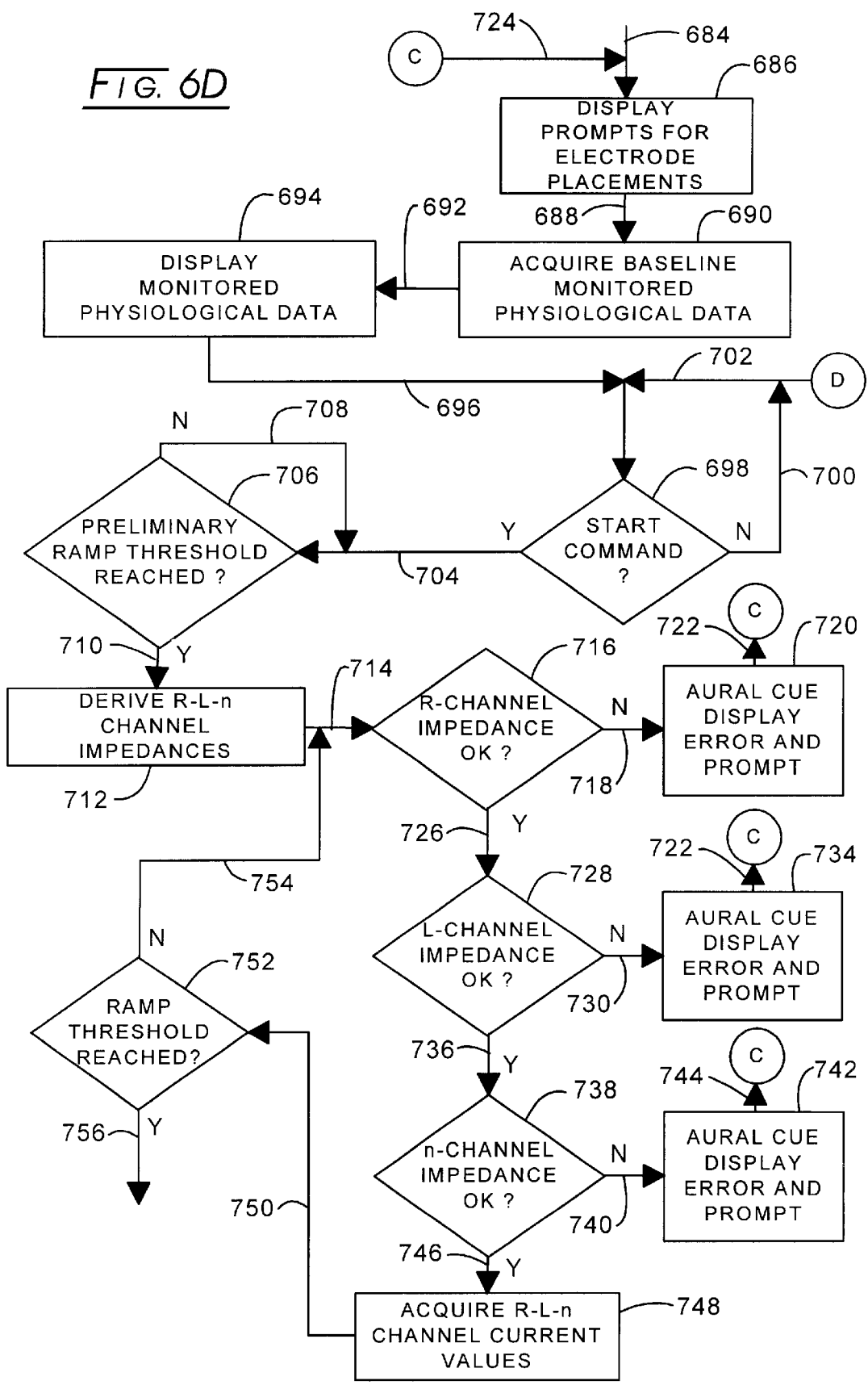

Line 684 reappears in FIG. 6D. Looking to that figure, the line is seen directed to block 686 which provides for the displaying of prompts instructing in the proper placement of the electrodes. Then, as represented at line 688 and block 690 the program acquires the starting or baseline monitored physiological data for the patient. It is from this baseline data that trends and the like can be evaluated to determine the physiological reaction to the treatment on the part of the patient. Then, as represented at line 692 and block 694 the program displays that physiological data which is being monitored. The program then continues as represented at line 696 and block 698 where a determination is made as to whether a start command has been received. In the event that a start signal has not occurred, then the program loops as represented by lines 700 and 702. With the presence of the start command, the program proceeds as represented at line 704 and block 706 at which a query is posed questioning whether a preliminary ramp threshold value has been reached. In this regard, during the ramping interval it is desirable to evaluate the load impedance for purposes as discussed above, i.e., for example, determining whether the electrodes are properly placed. Thus, the impedance of each channel is checked during the ramping process. Accordingly, when this preliminary threshold is reached, then as represented at line 710 and block 712 the impedances for each channel are derived. Then, as represented at line 714 and block 716, the program commences to evaluate the impedance for each channel. In block 17, a first channel, designated "R" is checked with respect to impedance. In the event that the impedance is improper, then as represented at line 718 and block 720 an aural cue is sounded. The error is set forth in a display and a prompt is provided advising the practitioner as to proper corrective procedure. The program then proceeds as represented by line 722 to node C which reappears with line 724 extending to line 684. Where the first channel impedance is appropriate, then as represented at line 726 and block 728 the second channel is checked for impedance, here designated as the "L" channel. Where that impedance if found to be improper, then, as represented at line 730 and block 732 the same form of aural cue occurs along with display prompts as described in connection with block 720, whereupon, as represented at line 734, the program reverts to node C as before. Where the second channel impedance is proper, then as represented at line 736 and block 738 any remaining channels are checked, the last herein being represented as channel "n". Block 738 provides for checking the impedance of channels through the last. In the event any one of those channels is defective in terms of impedance, then as represented at line 740 and block 742, an aural cue is sounded and the error is displayed with a prompt. As represented at line 744, the program then reverts to node C.

Where all channels are properly checked for impedance and all are exhibiting appropriate impedance values, then as represented at line 746 and block 748, the current values for each channel are acquired. Then, as represented at line 750 and block 752 a check is made as to whether the ramp target (threshold) value has been reached. In the event that it has not, then the program loops as represented at line 754. Where the ramp target (threshold) is reached, the program continues as represented at line 756.

Figure 6E:
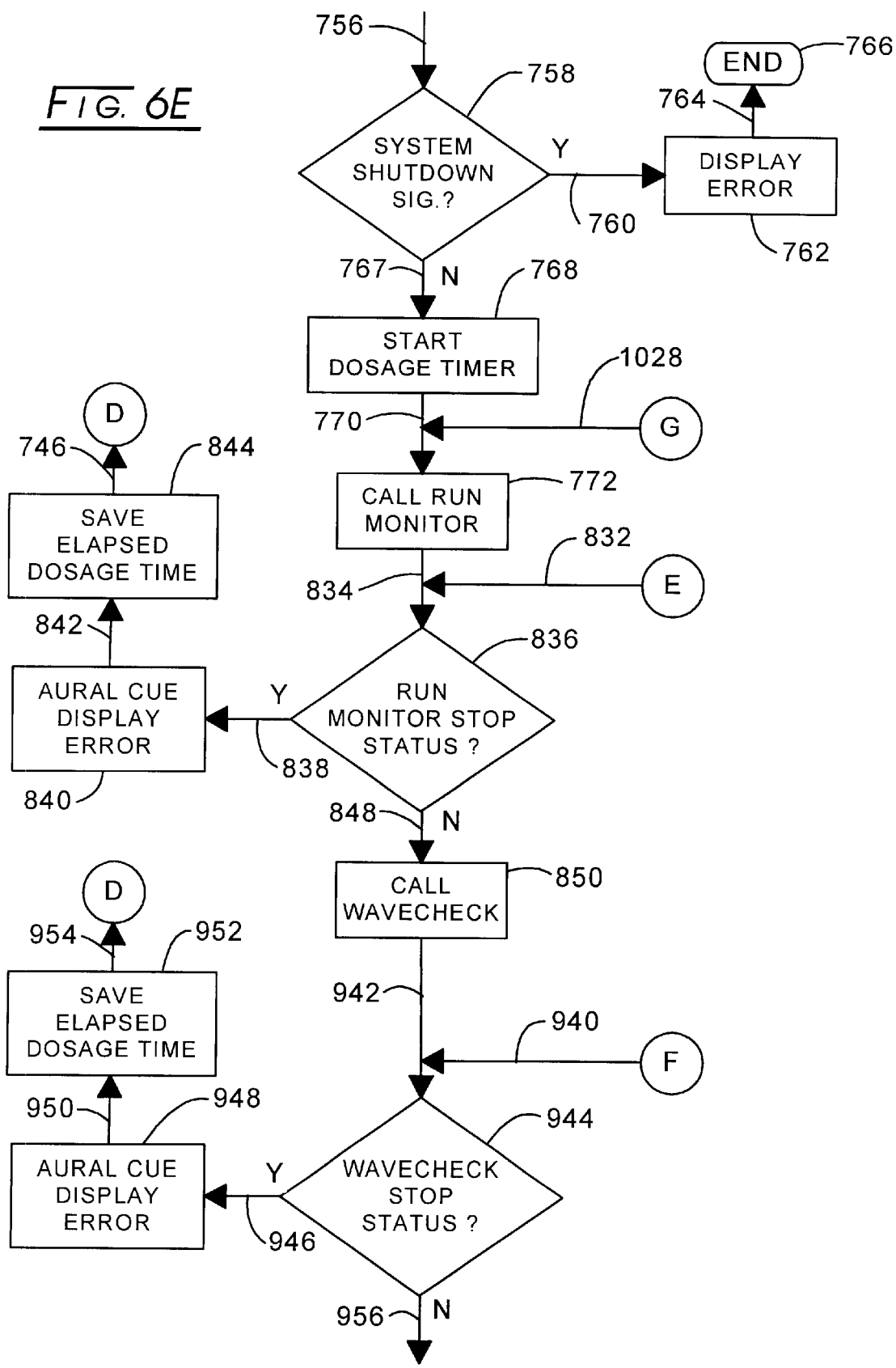

Referring to FIG. 6E, line 756 reappears extending to the query posed at block 758. That query determines whether or not a system shutdown signal has been received. It may be recalled from FIGS. 5A and 5B that the system incorporates an overcurrent detector and an overvoltage detector which are hard wired to develop a rapid shutdown. A system shutdown feature, in particular, was described at block 412 in FIG. 5A. Accordingly, when such a signal is received, as represented at line 760 and block 762 a shutdown error is displayed and, as represented at line 764 and node 766 the program is ended abruptly.

In the absence of a system shutdown, the program starts the dosage timer as represented at line 767 and block 768. Then, as represented at line 770 and block 772, a subroutine referred to as "run monitor" is called.

Figure 9:
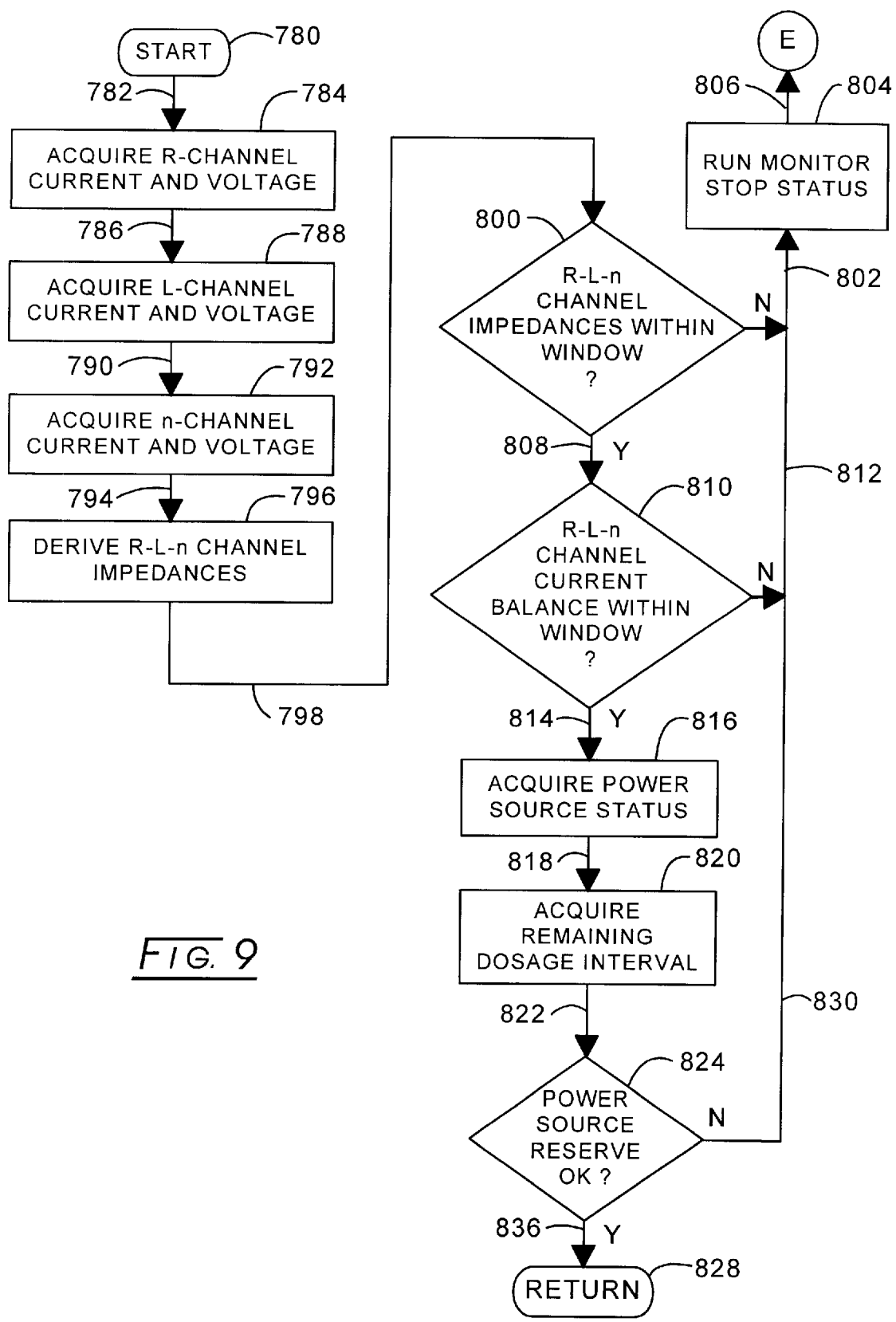
FIG. 9 is a flowchart showing a run monitor subroutine employed with the program represented at FIGS. 6A–6G.

Referring to FIG. 9, the run monitor subroutine is revealed. In the figure, the program commences at the start node 780 and, as represented at line 782 and block 784, the first channel current and voltage is acquired. Then, as represented at line 786 and 788, the second channel current and voltage values are acquired. In general, these values are acquired for all channels of the system through the nth channel. This is represented by line 790 and block 792 providing for the acquisition of the nth channel current and voltage values. The routine then continues as represented at line 794 and block 796 which provides for the derivation of the impedances of all channels. Then, as represented at line 798 and block 800 a determination is made as to whether all derived channel impedances fall within a window of acceptance. In the event one or more does not, then as represented at line 802 and block 804, a run monitor stop status signal is generated and the subroutine exits as represented at line 806 and node E.

In the event the channel impedances all fall within the appropriate window, then, as represented at line 808 and block 810 the balance of current between channels is checked and a determination is made as to whether any balance deficit falls outside a pre-selected window. In the event that any two channels fail to balance in terms of current, then, as represented at lines 812 and 802, the run monitor stop status signal is generated as represented at block 804. Where the channel current balance check is passed, then as represented at line 814 and block 816 the power source status is acquired. Acquiring this status becomes important where a battery power supply is utilized. Next, as represented at line 818 and block 820, the remaining dosage interval is acquired for purposes of evaluating the reserve of the power source or battery power supply. Accordingly, as represented at line 822 and block 824 a check is made of that power source reserve and, in the event it is appropriate to complete the dosage interval, as represented at line 826 and node 828 the subroutine returns to the main program. Where the power source reserve is not sufficient, then as represented at lines 830, 812, 802 and block 804, the noted run monitor stop status signal is generated, as represented at line 806 and node E.

Returning to FIG. 6E, node E reappears in conjunction with line 832 extending to line 834. Line 834 leads to the query posed at block 836 determining whether a run monitor stop signal has occurred. In the event that it has occurred, then as represented at line 838 and block 840, an aural cue is generated and an informational error signal is displayed. Then, as represented at line 842 and block 844 the elapsed dosage time is saved in memory and the program continues to node D. Node D reappears in FIG. 6D at line 702 extending to line 696, which in turn leads to block 698 where a start command is awaited.

Returning to FIG. 6E, where no run monitor stop status signal has been received, then as represented at line 848 and block 850 a subroutine referred to as "wavecheck" is called.

Figure 10:
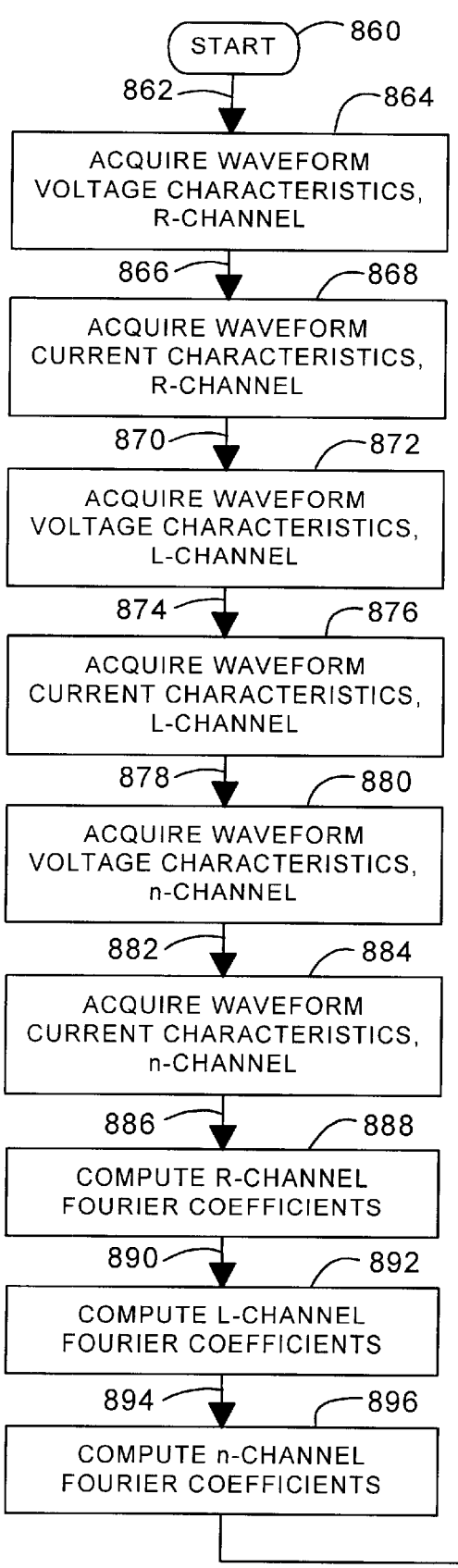
FIG. 10 is a flowchart describing a wavecheck subroutine employed by the program of FIGS. 6A–6G.
Figure 10:
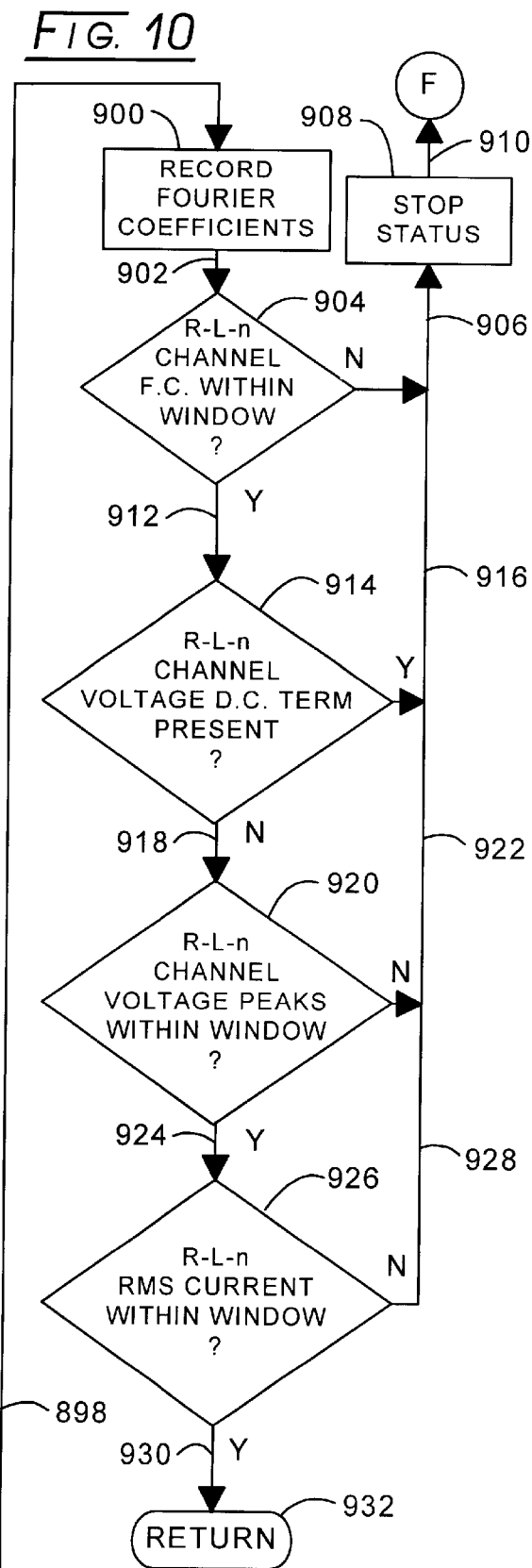

Referring to FIG. 10, the wavecheck subroutine is illustrated. In the figure, the subroutine commences with the start node 860 and line 862 leading to block 864. At block 864, instructions are provided for the acquisition of waveform voltage characteristics for the first channel. Those characteristics, in effect, identify the waveform. Next, as represented at line 866 and block 868, the corresponding waveform current characteristics for the first channel are acquired. These feedpoint current characteristics, as discussed above, will contain information or data relating to, inter alia, the impedance characteristics of the tissue region through which current is passing. Next, as represented at line 870 and block 872, the waveform voltage characteristics for the second channel are acquired. Then, as represented at line 874 and block 876 the waveform current characteristics for that second channel are acquired. These activities continue for all channels until the last or nth channel. That last channel waveform characteristic acquisition operation is represented at line 878 and block 880. Next, as represented at line 882 and block 884 the waveform current characteristics for the nth channel are acquired and the routine continues as represented at line 886. With the above acquisitions, data is available for analyzing the channel associated waveshapes. A variety of analyses may be carried out, for example, one analysis may provide for the determination of Fourier coefficients for each channel. Accordingly, as represented at block 888 such coefficients are computed for the first channel. Then, as represented at line 890 and block 892, the second channel Fourier coefficients are computed. Such computation of these coefficients is carried out for all channels in the system. The last such channel Fourier coefficient computation is accordingly represented at line 894 and block 896 calling for the computation of the nth channel Fourier coefficients. Inasmuch as it is quite desirable to retain and compile these computed coefficients, the routine then proceeds as represented at line 898 and block 900 providing for their recordation. The program then continues as represented at line 902 and block 904 to determine whether the computed Fourier coefficients for each channel fall within a predetermined coefficient window. In the event they do not, then, as represented at line 906 and block 908 a stop status signal is generated and directed as represented by line 910 and node F. Where the Fourier coefficients all fall within the appropriate window, the routine continues as is represented at line 912. At block 914 all channels are investigated for the presence of a d.c. term. Where such a d.c. term is present, then as represented by line 916 and block 908, a stop status signal is generated. Where no d.c. term is present in any channel, then as represented at line 918 and block 920 the voltage peaks for each channel are tested against window value. Where one or more of those voltage peaks is without the window, then as represented at lines 922, 916 and 906 leading to block 908, a stop status signal is generated. Where the tests posed at block 920 are met, then as represented at line 924 and block 926, the RMS current within each channel is tested against a window. Where that test is not met for one or more channels, then as represented at lines 928, 922, 916 and 906 as well as block 908, a stop status signal is generated. Where the tests posed at block 926 are met, then as represented at line 930 and node 932, the subroutine returns to the main program.

Node F appears in FIG. 6E. Returning to that figure, node F is seen extending to lines 940, 942 and block 944. At the latter block, a test is made as to whether a wavecheck stop status signal has been generated. Where such a signal has been generated, then as represented at line 946 and block 948 an aural cue is generated and the wavecheck error is displayed. Then, as represented at line 950 and block 952 the elapsed dosage time is saved in memory and the program reverts to node D as represented at line 954. Node D reappears in FIG. 6D in conjunction with line 702.

Returning to block 944, where a wavecheck stop status signal has not been received, then the program proceeds as represented at line 956.

Figure 6F:
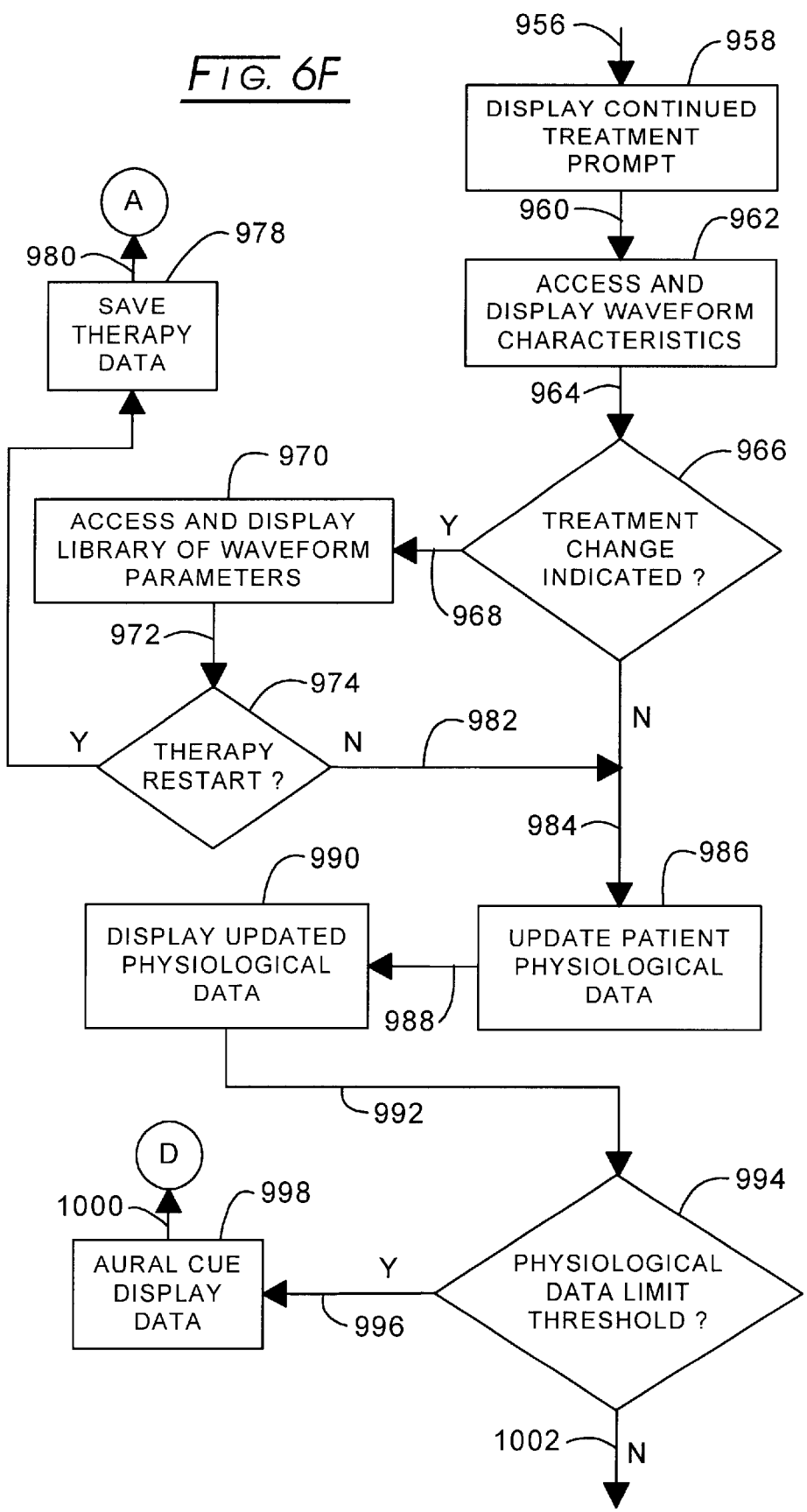

Referring to FIG. 6F, line 956 reappears in conjunction with block 958. This portion of the program is concerned with checking or reviewing the progress of therapeutic treatment while it is underway. Block 958 provides a display with continued treatment prompts describing the review procedure. Then, as represented by line 960 and block 962 a program accesses and displays the waveform characteristics thus far recorded in the course of the treatment. Then, as represented at line 964 and block 966 the program queries as to whether a treatment change has been indicated as desirable by the practitioner. In the event such change has been indicated, then as represented at line 968 and block 970 the practitioner is aided by the accessing and display from the memory library of waveform parameters which may be available for such a change. The program then progresses as represented at line 972 and block 974 wherein a query is made as to whether a therapy restart has been requested. In the event that it has been requested, then as represented at line 976 and block 978 the therapy data which heretofore has been recorded is saved and as represented at line 980 the program reverts to node A which appears at line 550 in FIG. 6A. Where the query posed at block 974 indicates that no therapy restart is indicated, then the program continues as represented at lines 982, 984 and block 978.

Returning to the query posed at block 966, where no treatment change has been indicated by the practitioner, then the program updates the patient physiological data as represented by line 984 and block 986. Following this update, as represented at line 988 and block 990 the updated physiological data is displayed and the program continues as represented at line 992 to the query posed at block 994. That query questions whether the physiological data limit threshold has been reached. In the event that it has, then as represented at line 996 and block 998 an aural cue is generated and the pertinent physiological data is displayed. Then, as represented at line 1000 the program reverts to node D which reappears in conjunction with line 702 in FIG. 6D. Where no physiological data limit threshold has been reached, then the program continues as represented at line 1002.

Figure 6G:
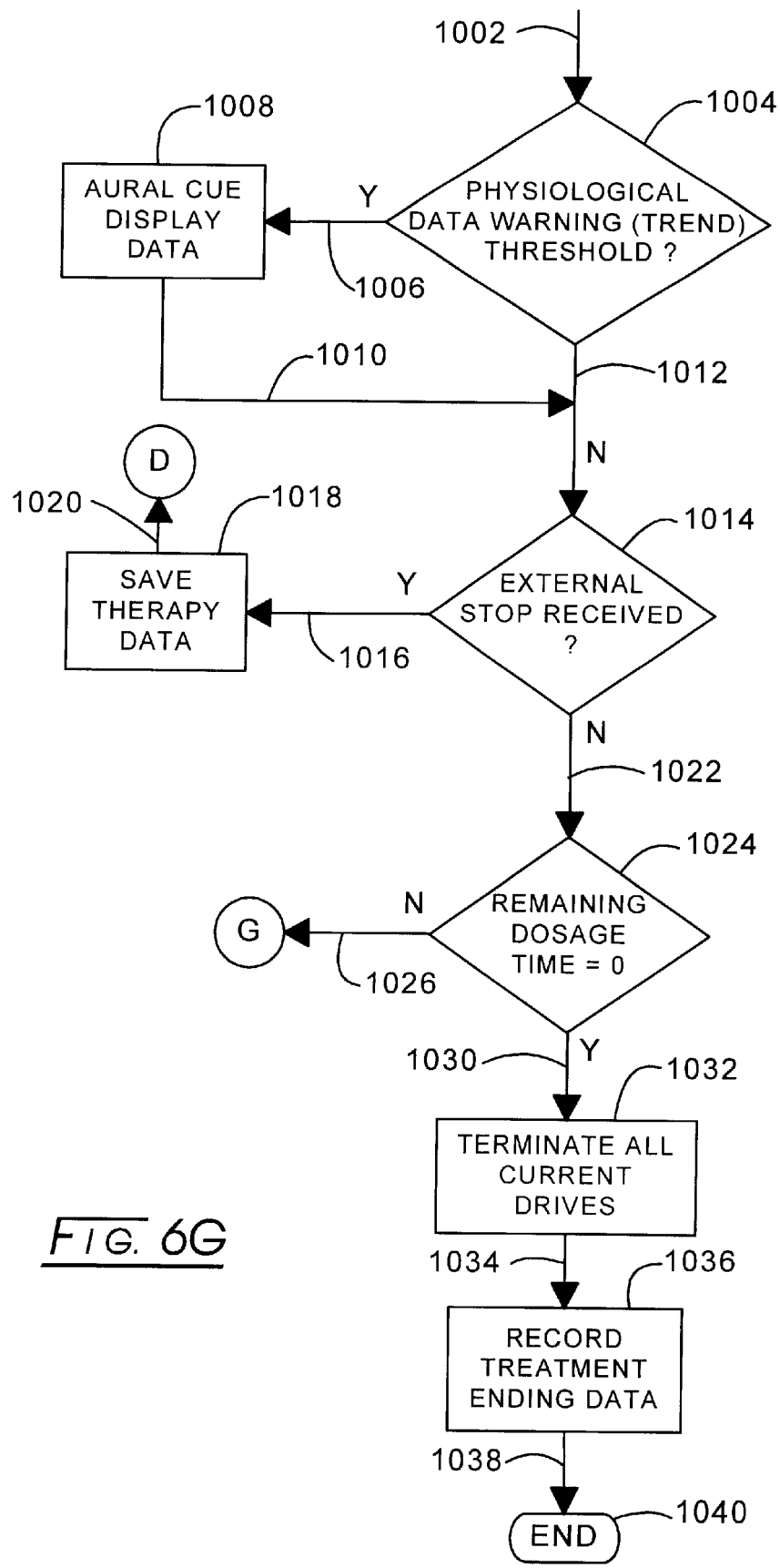

Line 1002 reappears in FIG. 6G extending to block 1004. The query posed at block 1004 determines whether a physiological data limit or trend analysis has reached a warning threshold. This means that enough change has been made in the physiology of the patient to merit bringing that change to the attention of the practitioner. In the event of a trend threshold being reached, as is represented at line 1006 and block 1008, an aural cue is generated and the trend data is displayed. The program then continues as represented at lines 1010 and 1012. Where the query posed at block 1004 indicates that no warning threshold has been reached, then, as represented at block 1014, the program queries as to whether an external stop has been received. In the event that such a stop has been received, as represented at line 1016 and block 1018 the therapy data is saved in memory and the program reverts to node D as represented at line 1020. Node D reappears in connection with FIG. 6D at line 702.

Where no external stop has been received, then as indicated at line 1022 and block 1024 a query is made as to whether the remaining dosage time is equal to zero. In the event that it is not, then as represented at line 1026 and node G the program loops. Node G reappears in FIG. 6E in conjunction with line 1028 extending to line 770. Where dosage time remains, then as represented at line 1030 and block 1032 all current drives to the electrodes are terminated and the program continues as represented at line 1034 and block 1036 which provides for the recordation of treatment ending data. The program then ends as represented at line 1038 and node 1040.

Figure 11:
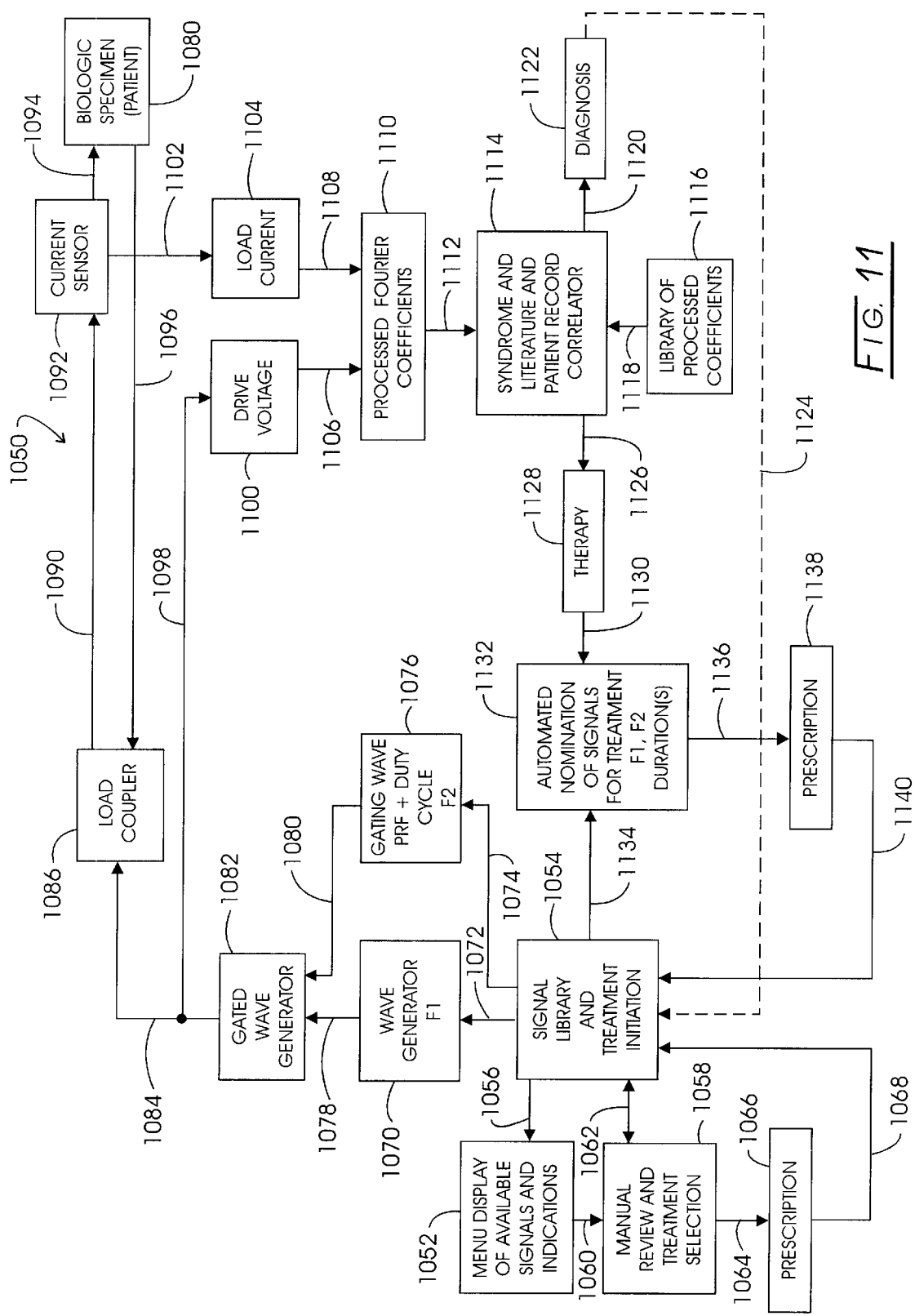
FIG. 11 is a block schematic diagram illustrating components and functions of a system for carrying out one version of diagnosis and therapy utilized by the system of the invention.

FIGS. 11 and 12 offer further demonstration of the flexibility of the instant system in carrying out diagnostic procedures to the extent of evoking research data and combining some aspects of that research and diagnosis in ongoing therapy. The latter approach is illustrated in connection with FIG. 11. Referring to that figure, a therapeutic and diagnostic system is represented generally at 1050. In general, system 1050 performs under the initial observation that a waveform can be applied to a load of variable and unknown impedance characteristics in a manner wherein electrical characteristics representing the load material, i.e., the human head, can be evolved and mathematically processed. System 1050 looks to a procedure wherein a conventionally utilized Limoge signal, at least in its rectangular wave format, initially is employed. In this regard, the higher frequency, F1, will be 167 kHz and the gating frequency will be 100 Hz. However, during the therapy that may change based upon a variety of diagnostic factors including mathematical processing of the feed point voltage and current waveforms.

In the figure, the practitioner is afforded a menu display of signals and indications which are available as represented at block 1052. Those available signals are derived from a signal library and treatment initiation function represented at block 1054 as represented at arrow 1056. Manual control for review and treatment selection is provided as represented at block 1058 and its association with display 1052 is represented at dual arrow 1060. Access to the library and for providing treatment initiation at block 1054 from the manual review function 1058 is represented at dual arrow 1062. Following practitioner review, the waveform (waveform parameters) is selected and, as represented at arrow 1064, a "prescription" is provided as represented at block 1066 which, as represented at arrow 1068 instructs the treatment initiation function at block 1054 as to the election of a particular waveform and treatment duration. At the commencement of a procedure, a more or less standard waveform as above described typically will be elected. Accordingly, treatment initiation at block 1054 provides for the enablement of a wave generator at the noted higher frequency, F1, as represented at bock 1070 and arrow 1072. Simultaneously, enablement is provided as represented by arrow 1074 to a gating function represented at block 1076 providing for a pulse repetition frequency (PRF) and duty cycle and presented at the frequency, F2. The output of wave generator 1070 and the gating output from control 1076 are provided, respectively, as represented by arrows 1078 and 1080 to a gated wave generator represented at block 1082. The resultant rectangular wave waveform output then is present at arrow 1084 which is seen to be introduced to a load coupler represented at block 1086. Load coupler 1086 is associated with the patient or biologic specimen represented at block 1088 through electrodes as earlier described and this association is represented by input arrow 1090 which is electrically operatively associated with a current sensing function represented at block 1092. The continuation of the output to electrical coupling with the patient 1080 is further represented at arrow 1094. An electrical return is represented in general by arrow 1096. Load coupler 1086 incorporates components functioning to optimize the coupling of the signal at arrow 1084 with the load represented at block 1080. Typically, this coupler function is implemented with a form of filter or LC network which can be automated in terms of handling the driving point source impedance at arrow 1084 in relation to the varying input impedances of the specimen 1080. Such coupler function 1086 may not be required in the event that the load impedance at hand is low enough and if the reactive component of the load is insignificant.

As described in connection with FIG. 1, the system 1050 is concerned with the difference between the waveform of the driving voltage and the resulting current waveform evoked as a consequence of current passing through the biologic specimen 1080. The squarewave drive voltage at arrow 1084 is tapped as represented at arrow 1098 and directed to a drive voltage signal conditioning function represented at block 1100. Similarly, the current proportional signal derived from the current sensor 1092 is tapped as represented at arrow 1102 which is directed to a load current signal conditioner represented at block 1104. Each waveform defining signal as represented at blocks 1100 and 1104 is directed, as represented by respective arrows 1106 and 1108 to a processing function represented at block 1110. For the present embodiment, that processing function includes the deriving of Fourier coefficients, such coefficients representing a mathematical description of the electrical form of waves, typically assigning amplitude and phase relationship with respect to frequency components of a wave. For the present embodiment, the processing involved develops Fourier coefficient differences, the amount of such a difference being related to the impedance characteristics at the specimen 1080. These difference values are sometimes referred to as differential coefficients. The data, now in digital form, derived at block 1110 is directed, as represented at arrow 1112 to a correlator function represented at block 1114. This correlation function receives the processed coefficient data as represented at arrow 1112 as well as data from a library of mathematically processed coefficients represented at 1116 and arrow 1118. Library function 1116 represents data from a population of patients correlating coefficient differences, for example, with syndrome records of that patient population.

The correlation can, for example, utilizing techniques of artificial intelligence and the like evolve a diagnosis as to the physical status of the patient 1080. That diagnosis is represented at arrow 1120 and block 1122. The resultant diagnosis is provided, along with corresponding signal data to the signal library function at block 1054 as represented by the dashed arrow 1124.

Additionally, as represented at arrow 1126 and block 1128 from the Fourier coefficients, a therapeutic waveshape can be identified and ultimately reconstructed. That data is presented as represented at arrow 1130 to a nomination of signals for treatment function, in effect, constructing the frequency F1, F2, durations. That function is represented at block 1132 which also responds to treatment initiation enablement ultimately developed from the manual selection function 1058 and represented as being asserted via arrow 1134. The output of the nomination function 1132 is represented at arrow 1136 and prescription block 1138, the data from which is asserted to the treatment initiation function 1054 as represented at arrow 1140.

The system of the invention can be utilized with a variety of electrical stimuli applied to the patient through the electrodes which, in turn, may be varied to evolve a diagnostic form of data. In this regard, the diagnostic stimulus is applied; responses are measured and recorded; and characteristics are calculated and recorded. FIG. 12 looks to a sweep frequency implementation of this diagnostic approach. Looking to the figure, the system is revealed in general at 1150 to be implemented with an interrogation program represented at block 1152. The underlying tenet of the waveform utilized resides in the requirement that no deleterious d.c. term be present in the waveform applied. The interrogation program 1152 carries out a sweep of frequencies in a predetermined zone of frequencies at the earlier-noted higher frequency, F1. The program also may sweep within a zone of gating frequencies, F2. Further, the amplitudes of the positive-going and negative-going components of the waveforms developed in this sweep function, may be adjusted within the confines of the zero d.c. term criterion. Interrogation program 1152 provides a control to a wave generator at the higher, F1, frequency as represented at arrow 1154 and block 1156. Similarly, an interrogation control is asserted to a gating wave PRF and duty cycle corresponding with frequency F2 as represented at block 1158 and arrow 1160. The resultant output of generator 1156 is asserted, as represented at arrow 1162, to a gated wave generator function represented at block 1164. The gating feature of that generator function 1164 is provided from block 1158 as represented at arrow 1166. In carrying out a sweep frequency analysis, waveshapes for a sequence within a range defined between starting and ending frequencies would be asserted in timed sequential fashion to generator 1164 in combination with corresponding gating wave data as represented at arrow 1166. Additionally, the frequency asserted from arrow 1162 can be stabilized and the gating data from arrow 1166 can be swept in a range or zone extant between beginning and ending gating data signals.

As before, the rectangular wave output from the generator function at block 1164 is asserted as represented at arrow 1168. The sweep frequency range of application generally will be provided as zones which will fall within boundaries of about 100 kHz up to about 10 mHz, while the burst frequencies, F2 generally will fall within ranges which are, in turn, within bounds of about 10 Hz to one kHz. These sweep signals asserted at arrow 1168, as before, are introduced to a load coupler function represented at block 1170. Coupler 1170 has the function described above in connection with block 1086. The drive output from coupler 1170 is represented at arrow 1172 through the current sensing function represented at block 1174 and then, as represented at arrow 1176 and block 1178 through an electrode to the biologic specimen or patient. The return from the corresponding electrode at the patient 1178 is represented in general by the arrow 1180.

As before, the rectangular wave evolved voltage waveform at arrow 1168 is tapped as represented at arrow 1182 and signal conditioned as represented at block 1184 to provide a scaled signal corresponding with the drive voltage waveform as represented at arrow 1186. The output of the current sensor 1174 is directed as represented at arrow 1188 to a load current signal treatment component represented at block 1190 to provide a corresponding waveform defining output represented at arrow 1192. As before, that output and the output at arrow 1186 are processed as represented at block 1193 to provide corresponding Fourier coefficients. Digital data representing those coefficients is submitted, as represented by arrow 1194, to a correlator function represented at block 1196. Note, that for system 1150, the correlator function 1196 is receiving sweep frequency data for compilation and analysis. Generally, from that data, the correlator function 1196 looks for anomalies in the frequency-response energy transfer characteristics of the biologic specimen or patient 1178. As before, by reference to the driving rectangular wave characterized voltage waveform difference or differential data can be evolved. Resistive impedance characteristics as well as reactive impedance characteristics of the analyzed specimen at 1178 are available with the system. This body of data for each patient is submitted to memory for the purpose of evolving an associated database carrying patient data and the noted wave coefficients and processed coefficients. This database is represented generally at 1198 and for illustrative purposes is represented by "Patient Data 1" block 1200; "Patient Data 2" block 1201 and that patient data collection will continue until an nth or last inserted "Patient Data" collection represented in block 1202 as patient data n. The outputs from block 1200–1202 are shown respectively at 1204–1206 being directed to the correlator function 1196. Function 1196, as represented at arrow 1208 and dashed block 1210 may employ coefficient input from arrow 1194 as well as data from the database 1198 to carry out a predictive diagnosis for comparison with other tests. Such diagnoses predict that other tests may well verify the condition predicted by the correlator function 1196. On the other hand, an enhanced diagnosis in time and scope may be developed wherein, due to substantial database experience evolved from the data extent of the database 1198, a diagnosis of high probability can be outputted. Such data base management procedures as involve artificial intelligence and/or neural networking may be employed to achieve this enhanced diagnostic procedure.

Since certain changes may be made in the above-described apparatus, system and method without departing from the scope of the invention herein involved, it is intended that all matter contained in the description thereof or shown in the accompanying drawings shall be interpreted as illustrative and not in a limiting sense.

What is claimed is:

1. Apparatus for applying electrical current to an animal having spaced apart skin surface regions spanning a tissue volume exhibiting biologically-based electrical impedances, comprising:

an application assembly having a first electrode assembly of first designated polarity positionable for electrical communication at a first region of said skin and a second electrode assembly of second designated polarity positionable for electrical communication at a second region of said skin remote from said first region;

said application assembly first electrode assembly including a first channel electrode locatable at a first channel position of said first region of said skin, and a second channel electrode locatable at a second channel position of said first region of said skin spaced from said first channel position;

electrical generation apparatus including first and second terminals electrically coupled with respective said first and second electrode assemblies and actuable in response to a start input to generate electrical excitation outputs across said first and second terminals exhibiting select frequencies and waveshapes having given electrical characteristics, further responsive at the commencement of said start input to generate said electrical outputs at progressively increasing values of voltage and current and thereafter responsive to a ramp target signal to generate predetermined values of said voltage and current with corresponding said waveshapes, and responsive to a stop input to terminate said electrical outputs;

said electrical generation apparatus electrical excitation outputs including a first channel output coupled in electrical communication through said first terminal output to said first channel electrode and a second channel output coupled in electrical communication through said first terminal output to said second channel electrode;

a current sensor assembly responsive to said electrical excitation outputs for providing a monitored current value output;

said current sensor assembly including a first channel current sensor responsive to said first channel output for providing said monitored current value output as a first channel monitored current value output, and a second channel current sensor responsive to said second channel output for providing said monitored current value output as a second channel monitored current value output;

a voltage sensor assembly responsive to said electrical excitation outputs for providing a monitored voltage value output;

said voltage sensor assembly including a first channel voltage sensor responsive to said first channel output for providing said monitored voltage value output as a first channel monitored voltage value output, and a second channel voltage sensor responsive to said second channel output for providing said monitored voltage value output as a second channel monitored voltage value output;

a control assembly including a control input for receiving a time interval of application input and start and stop actuations, said control assembly being responsive to a said start actuation to derive said start input and to said stop actuation to derive said stop input, responsive to said monitored current value output, to said monitored voltage value output, and to a predetermined load impedance value for deriving an impedance fault signal when said monitored current value output and said monitored voltage value output represent an impedance not corresponding with said predetermined load impedance value, responsive to at least one said monitored current value output and monitored voltage value output and to a predetermined electrical ramp parameter target value to derive said ramp target signal, responsive to said monitored current value output and to a predetermined overcurrent threshold value to derive a said stop input when said monitored current value output exceeds said predetermined overcurrent threshold value, responsive to said monitored voltage value output and to a predetermined overvoltage value to derive a said stop signal when said monitored voltage value input exceeds said predetermined overvoltage value, and responsive to said start input, said ramp threshold signal and to said time interval of application input for deriving said stop input at the termination of said time interval of application;

said control assembly being responsive to said first channel monitored current value output, said first channel monitored voltage value output and to said predetermined load impedance value for deriving a first channel designated fault signal when said first channel monitored current value output and said first channel monitored voltage output represents a said impedance not corresponding with said predetermined load impedance, said control assembly being responsive to said second channel monitored current value output and said second channel monitored voltage value output and to said predetermined load impedance value for deriving a second channel designated fault signal when said second channel monitored current value output and said second channel monitored voltage output represents a said impedance not corresponding with said predetermined load impedance;

said control assembly further comprising a display assembly providing third perceptible indicia in the presence of a balance fault signal;

said control assembly being responsive to said electrical generation apparatus waveshapes present at said first channel output and said second channel output and is being further responsive to compare predetermined ones of said given electrical characteristics of said waveshapes at said first and second channel outputs to derive a balance value; and said control assembly being responsive to compare said balance value with a predetermined balance limit value, and being further responsive to derive a said balance fault signal when said balance value exceeds said predetermined balance limit value.

2. Apparatus for applying electrical current to an animal having spaced apart skin surface regions spanning a tissue volume exhibiting biologically-based electrical impedances, comprising:

an application assembly having a first electrode assembly of first designated polarity positionable for electrical communication at a first region of said skin and a second electrode assembly of second designated polarity positionable for electrical communication at a second region of said skin remote from said first region;

said application assembly first electrode assembly including a first channel electrode locatable at a first channel position of said first region of said skin, and a second channel electrode locatable at a second channel position of said first region of said skin spaced from said first channel position;

electrical generation apparatus including first and second terminals electrically coupled with respective said first and second electrode assemblies and actuable in response to a start input to generate electrical excitation outputs across said first and second terminals exhibiting select frequencies and waveshapes having given electrical characteristics , further responsive at the commencement of said start input to generate said electrical outputs at progressively increasing values of voltage and current and thereafter responsive to a ramp target signal to generate predetermined values of said voltage and current with corresponding said waveshapes, and responsive to a stop input to terminate said electrical outputs;

said electrical generation apparatus electrical excitation outputs including a first channel output coupled in electrical communication through said first terminal output to said first channel electrode and a second channel output coupled in electrical communication through said first terminal output to said second channel electrode;

a current sensor assembly responsive to said electrical excitation outputs for providing a monitored current value output;

said current sensor assembly including a first channel current sensor responsive to said first channel output for providing said monitored current value output as a first channel monitored current value output, and a second channel current sensor responsive to said second channel output for providing said monitored current value output as a second channel monitored current value output;

a voltage sensor assembly responsive to said electrical excitation outputs for providing a monitored voltage value output;

said voltage sensor assembly including a first channel voltage sensor responsive to said first channel output for providing said monitored voltage value output as a first channel monitored voltage value output, and a second channel voltage sensor responsive to said second channel output for providing said monitored voltage value output as a second channel monitored voltage value output;

a control assembly including a control input for receiving a time interval of application input and start and stop actuations, said control assembly being responsive to a said start actuation to derive said start input and to said stop actuation to derive said stop input, responsive to said monitored current value output, to said monitored voltage value output, and to a predetermined load impedance value for deriving an impedance fault signal when said monitored current value output and said monitored voltage value output represent an impedance not corresponding with said predetermined load impedance value, responsive to at least one said monitored current value output and monitored voltage value output and to a predetermined electrical ramp parameter target value to derive said ramp target signal, responsive to said monitored current value output and to a predetermined overcurrent threshold value to derive a said stop input when said monitored current value output exceeds said predetermined overcurrent threshold value, responsive to said monitored voltage value output and to a predetermined overvoltage value to derive a said stop signal when said monitored voltage value input exceeds said predetermined overvoltage value, and responsive to said start input, said ramp threshold signal and to said time interval of application input for deriving said stop input at the termination of said time interval of application;

said control assembly being responsive to said first channel monitored current value output, said first channel monitored voltage value output and to said predetermined load impedance value for deriving a first channel designated fault signal when said first channel monitored current value output and said first channel monitored voltage output represents a said impedance not corresponding with said predetermined load impedance, said control assembly being responsive to said second channel monitored current value output and said second channel monitored voltage value output and to said predetermined load impedance value for deriving a second channel designated fault signal when said second channel monitored current value output and said second channel monitored voltage output represents a said impedance not corresponding with said predetermined load impedance;

said control assembly further comprising a display assembly providing third perceptible indicia in the presence of a balance fault signal;

said control assembly being responsive to a peak value of said first channel monitored current value output and to corresponding peak value of said second channel monitored current value output to derive a peak current difference value as the difference between them, and is responsive to a predetermined peak current balance limit value and to said peak current difference value to derive a said balance fault signal when said peak current balance value exceeds said predetermined peak current balance limit value.

3. Apparatus for applying electrical current to an animal having spaced apart skin surface regions spanning a tissue volume exhibiting biologically-based electrical impedances, comprising:

an application assembly having a first electrode assembly of first designated polarity positionable for electrical communication at a first region of said skin and a second electrode assembly of second designated polarity positionable for electrical communication at a second region of said skin remote from said first region;

said application assembly first electrode assembly including a first channel electrode locatable at a first channel position of said first region of said skin, and a second channel electrode locatable at a second channel position of said first region of said skin spaced from said first channel position;

electrical generation apparatus including first and second terminals electrically coupled with respective said first and second electrode assemblies and actuable in response to a start input to generate electrical excitation outputs across said first and second terminals exhibiting select frequencies and waveshapes having given electrical characteristics, further responsive at the commencement of said start input to generate said electrical outputs at progressively increasing values of voltage and current and thereafter responsive to a ramp target signal to generate predetermined values of said voltage and current with corresponding said waveshapes, and responsive to a stop input to terminate said electrical outputs;

said electrical generation apparatus electrical excitation outputs including a first channel output coupled in electrical communication through said first terminal output to said first channel electrode and a second channel output coupled in electrical communication through said first terminal output to said second channel electrode;

a current sensor assembly responsive to said electrical excitation outputs for providing a monitored current value output;

said current sensor assembly including a first channel current sensor responsive to said first channel output for providing said monitored current value output as a first channel monitored current value output, and a second channel current sensor responsive to said second channel output for providing said monitored current value output as a second channel monitored current value output;

a voltage sensor assembly responsive to said electrical excitation outputs for providing a monitored voltage value output;

said voltage sensor assembly including a first channel voltage sensor responsive to said first channel output for providing said monitored voltage value output as a first channel monitored voltage value output, and a second channel voltage sensor responsive to said second channel output for providing said monitored voltage value output as a second channel monitored voltage value output;

a control assembly including a control input for receiving a time interval of application input and start and stop actuations, said control assembly being responsive to a said start actuation to derive said start input and to said stop actuation to derive said stop input, responsive to said monitored current value output, to said monitored voltage value output, and to a predetermined load impedance value for deriving an impedance fault signal when said monitored current value output and said monitored voltage value output represent an impedance not corresponding with said predetermined load impedance value, responsive to at least one said monitored current value output and monitored voltage value output and to a predetermined electrical ramp parameter target value to derive said ramp target signal, responsive to said monitored current value output and to a predetermined overcurrent threshold value to derive a said stop input when said monitored current value output exceeds said predetermined overcurrent threshold value, responsive to said monitored voltage value output and to a predetermined overvoltage value to derive a said stop signal when said monitored voltage value input exceeds said predetermined overvoltage value, and responsive to said start input, said ramp threshold signal and to said time interval of application input for deriving said stop input at the termination of said time interval of application;

said control assembly being responsive to said first channel monitored current value output, said first channel monitored voltage value output and to said predetermined load impedance value for deriving a first channel designated fault signal when said first channel monitored current value output and said first channel monitored voltage output represents a said impedance not corresponding with said predetermined load impedance, said control assembly being responsive to said second channel monitored current value output and said second channel monitored voltage value output and to said predetermined load impedance value for deriving a second channel designated fault signal when said second channel monitored current value output and said second channel monitored voltage output represents a said impedance not corresponding with said predetermined load impedance;

said control assembly further comprising a display assembly providing third perceptible indicia in the presence of a balance fault signal; and said control assembly being responsive to a peak value of said first channel monitored voltage value output and to a corresponding peak value of said second channel monitored voltage value to derive a peak voltage difference value as the difference between them, and being responsive to a predetermined peak voltage balance limit value and to said peak voltage balance limit value to derive a said balance fault signal when said peak voltage balance value exceeds said predetermined peak voltage balance limit value.

4. Apparatus for applying electrical current to an animal having spaced apart skin surface regions spanning a tissue volume exhibiting biologically-based electrical impedances, comprising:

an application assembly having a first electrode assembly of first designated polarity positionable for electrical communication at a first region of said skin and a second electrode assembly of second designated polarity positionable for electrical communication at a second region of said skin remote from said first region;

electrical generation apparatus including first and second terminals electrically coupled with respective said first and second electrode assemblies and actuable in response to a start input to generate electrical excitation outputs across said first and second terminals exhibiting select frequencies and waveshapes having given electrical characteristics, further responsive at the commencement of said start input to generate said electrical outputs at progressively increasing values of voltage and current and thereafter responsive to a ramp target signal to generate predetermined values of said voltage and current with corresponding said waveshapes, and responsive to a stop input to terminate said electrical outputs;

a current sensor assembly responsive to said electrical excitation outputs for providing a monitored current value output;

a voltage sensor assembly responsive to said electrical excitation outputs for providing a monitored voltage value output;

a control assembly including a control input for receiving a time interval of application input and start and stop actuations, said control assembly being responsive to a said start actuation to derive said start input and to said stop actuation to derive said stop input, responsive to said monitored current value output, to said monitored voltage value output, and to a predetermined load impedance value for deriving an impedance fault signal when said monitored current value output and said monitored voltage value output represent an impedance not corresponding with said predetermined load impedance value, responsive to at least one said monitored current value output and monitored voltage value output and to a predetermined electrical ramp parameter target value to derive said ramp target signal, responsive to said monitored current value output and to a predetermined overcurrent threshold value to derive a said stop input when said monitored current value output exceeds said predetermined overcurrent threshold value, responsive to said monitored voltage value output and to a predetermined overvoltage value to derive a said stop signal when said monitored voltage value input exceeds said predetermined overvoltage value, and responsive to said start input, said ramp threshold signal and to said time interval of application input for deriving said stop input at the termination of said time interval of application;

said predetermined load impedance value being represented as a first acceptable increasing range of voltage and corresponding current values, and a second range of increasing acceptable voltage and corresponding current values, the rate of increase of said current values of said first range being greater than the rate of increase of said current values of said second range; and said control assembly deriving said impedance fault signal as an electrode fault signal when, for any given value of voltage of both said first and second range, the value of current is less than the corresponding acceptable value of current of said second range.

5. The apparatus of claim 4 in which:

said control assembly derives said impedance fault signal as a current fault signal when, for any given value of voltage of both said first and second range, the value of current is greater than the corresponding acceptable value of current of said first range.

6. Apparatus for applying electrical current to an animal having spaced apart skin surface regions spanning a tissue volume exhibiting biologically-based electrical impedances, comprising:

an application assembly having a first electrode assembly of first designated polarity positionable for electrical communication at a first region of said skin and a second electrode assembly of second designated polarity positionable for electrical communication at a second region of said skin remote from said first region;

said application assembly first electrode assembly including a first channel electrode locatable at a first channel position of said first region of said skin, and a second channel electrode locatable at a second channel position of said first region of said skin spaced from said first channel position;

electrical generation apparatus including first and second terminals electrically coupled with respective said first and second electrode assemblies and actuable in response to a start input to generate electrical excitation outputs across said first and second terminals exhibiting select frequencies and waveshapes having given electrical characteristics , further responsive at the commencement of said start input to generate said electrical outputs at progressively increasing values of voltage and current and thereafter responsive to a ramp target signal to generate predetermined values of said voltage and current with corresponding said waveshapes, and responsive to a stop input to terminate said electrical outputs;

said electrical generation apparatus electrical excitation outputs including a first channel output coupled in electrical communication through said first terminal output to said first channel electrode and a second channel output coupled in electrical communication through said first terminal output to said second channel electrode;

said electrical generation apparatus further comprising:

a first channel ramp generator actuable to provide a first ramp signal of given instantaneous amplitudes;

a first channel positive voltage converter responsive to said first ramp signal to provide a first positive-going output exhibiting a positive voltage amplitude corresponding with said first ramp signal amplitudes a first channel negative voltage converter responsive to said first ramp signal to provide a first negative-going output exhibiting a negative voltage amplitude corresponding with said first ramp signal amplitudes a first channel output driver responsive to said first positive-going output and to said first negative-going output and controllable to derive a first waveform as a combination thereof occurring with a first frequency f1, and with a burst repetition at a second frequency f2, of value less than said frequency, f1, as said first channel output;

a second channel ramp generator actuable to provide a second ramp signal of given instantaneous amplitudes;

a second channel positive voltage converter responsive to said second ramp signal to provide a positive-going output exhibiting a positive voltage responsive to said second ramp signal to provide a positive-going output exhibiting a positive voltage amplitude corresponding with said second ramp signal amplitude;

a second channel negative voltage converter responsive to said second ramp signal to provide a negative-going output exhibiting a negative voltage amplitude corresponding with said second ramp amplitudes;

a second channel output driver responsive to said second positive-going output and to said second negative-going output and controllable to derive a second waveform as a combination thereof occurring with a first frequency f1, and at said burst repetition second frequency f2, as said second channel output;

a waveform generator responsive to said start input for controlling said first and second channel output drivers;

a current sensor assembly responsive to said electrical excitation outputs for providing a monitored current value output;

said current sensor assembly including a first channel current sensor responsive to said first channel output for providing said monitored current value output as a first channel monitored current value output, and a second channel current sensor responsive to said second channel output for providing said monitored current value output as a second channel monitored current value output;

a voltage sensor assembly responsive to said electrical excitation outputs for providing a monitored voltage value output;

said voltage sensor assembly including a first channel voltage sensor responsive to said first channel output for providing said monitored voltage value output as a first channel monitored voltage value output, and a second channel voltage sensor responsive to said second channel output for providing said monitored voltage value output as a second channel monitored voltage value output;

a control assembly including a control input for receiving a time interval of application input and start and stop actuations, said control assembly being responsive to a said start actuation to derive said start input and to said stop actuation to derive said stop input, responsive to said monitored current value output, to said monitored voltage value output, and to a predetermined load impedance value for deriving an impedance fault signal when said monitored current value output and said monitored voltage value output represent an impedance not corresponding with said predetermined load impedance value, responsive to at least one said monitored current value output and monitored voltage value output and to a predetermined electrical ramp parameter target value to derive said ramp target signal, responsive to said monitored current value output and to a predetermined overcurrent threshold value to derive a said stop input when said monitored current value output exceeds said predetermined overcurrent threshold value, responsive to said monitored voltage value output and to a predetermined overvoltage value to derive a said stop signal when said monitored voltage value input exceeds said predetermined overvoltage value, and responsive to said start input, said ramp threshold signal and to said time interval of application input for deriving said stop input at the termination of said time interval of application; and said control assembly being responsive to said first channel monitored current value output, said first channel monitored voltage value output and to said predetermined load impedance value for deriving a first channel designated fault signal when said first channel monitored current value output and said first channel monitored voltage output represents a said impedance not corresponding with said predetermined load impedance, said control assembly being responsive to said second channel monitored current value output and said second channel monitored voltage value output and to said predetermined load impedance value for deriving a second channel designated fault signal when said second channel monitored current value output and said second channel monitored voltage output represents a said impedance not corresponding with said predetermined load impedance.

7. Apparatus for applying electrical current to an animal having spaced apart skin surface regions spanning a tissue volume exhibiting biologically-based electrical impedances, comprising:

an application assembly having a first electrode assembly of first designated polarity positionable for electrical communication at a first region of said skin and a second electrode assembly of second designated polarity positionable for electrical communication at a second region of said skin remote from said first region;

electrical generation apparatus including first and second terminals electrically coupled with respective said first and second electrode assemblies and actuable in response to a start input to generate electrical excitation outputs across said first and second terminals exhibiting select frequencies and waveshapes having no d.c. term effective to derive iontophoresis and having given electrical characteristics, further responsive at the commencement of said start input to generate said electrical outputs at progressively increasing values of voltage and current and thereafter responsive to a ramp target signal to generate predetermined values of said voltage and current with corresponding said waveshapes, and responsive to a stop input to terminate said electrical outputs;

a current sensor assembly responsive to said electrical excitation outputs for providing a monitored current value output;

a voltage sensor assembly responsive to said electrical excitation outputs for providing a monitored voltage value output;

a d.c. offset detector assembly responsive to said electrical excitation outputs for providing a d.c. term value output a control assembly including a control input for receiving a time interval of application input and start and stop actuations, said control assembly being responsive to a said start actuation to derive said start input and to said stop actuation to derive said stop input, responsive to said monitored current value output, to said monitored voltage value output, and to a predetermined load impedance value for deriving an impedance fault signal when said monitored current value output and said monitored voltage value output represent an impedance not corresponding with said predetermined load impedance value, responsive to at least one said monitored current value output and monitored voltage value output and to a predetermined electrical ramp parameter target value to derive said ramp target signal, responsive to said monitored current value output and to a predetermined overcurrent threshold value to derive a said stop input when said monitored current value output exceeds said predetermined overcurrent threshold value, responsive to said monitored voltage value output and to a predetermined overvoltage value to derive a said stop signal when said monitored voltage value input exceeds said predetermined overvoltage value, and responsive to said start input, said ramp threshold signal and to said time interval of application input for deriving said stop input at the termination of said time interval of application; and said control assembly is responsive to said d.c. term value output, and to a predetermined d.c. term limit of value effective to avoid iontopharesis to derive a said stop input when said d.c. term value output exceeds said predetermined d.c. term limit.

8. Apparatus for applying electrical current to an animal having spaced apart skin surface regions spanning a tissue volume exhibiting biologically-based electrical impedances, comprising:

an application assembly having a first electrode assembly of first designated polarity positionable for electrical communication at a first region of said skin and a second electrode assembly of second designated polarity positionable for electrical communication at a second region of said skin remote from said first region;

said application assembly first electrode assembly including a first channel electrode locatable at a first channel position of said first region of said skin, and a second channel electrode locatable at a second channel position of said first region of said skin spaced from said first channel position;

electrical generation apparatus including first and second terminals electrically coupled with respective said first and second electrode assemblies and actuable in response to a start input to generate electrical excitation outputs across said first and second terminals exhibiting select frequencies and waveshapes having no d.c. term effective to derive iontophoresis and having given electrical characteristics, further responsive at the commencement of said start input to generate said electrical outputs at progressively increasing values of voltage and current and thereafter responsive to a ramp target signal to generate predetermined values of said voltage and current with corresponding said waveshapes, and responsive to a stop input to terminate said electrical outputs;

said electrical generation apparatus electrical excitation outputs including a first channel output coupled in electrical communication through said first terminal output to said first channel electrode and a second channel output coupled in electrical communication through said first terminal output to said second channel electrode;

a current sensor assembly responsive to said electrical excitation outputs for providing a monitored current value output;

said current sensor assembly including a first channel current sensor responsive to said first channel output for providing said monitored current value output as a first channel monitored current value output, and a second channel current sensor responsive to said second channel output for providing said monitored current value output as a second channel monitored current value output;

said current sensor assembly including a second electrode current sensor responsive to said electrical outputs corresponding with said second electrode assembly for providing a second electrode designated monitored current value output;

a voltage sensor assembly responsive to said electrical excitation outputs for providing a monitored voltage value output;

said voltage sensor assembly including a first channel voltage sensor responsive to said first channel output for providing said monitored voltage value output as a first channel monitored voltage value output, and a second channel voltage sensor responsive to said second channel output for providing said monitored voltage value output as a second channel monitored voltage value output;

a control assembly including a control input for receiving a time interval of application input and start and stop actuations, said control assembly being responsive to a said start actuation to derive said start input and to said stop actuation to derive said stop input, responsive to said monitored current value output, to said monitored voltage value output, and to a predetermined load impedance value for deriving an impedance fault signal when said monitored current value output and said monitored voltage value output represent an impedance not corresponding with said predetermined load impedance value, responsive to at least one said monitored current value output and monitored voltage value output and to a predetermined electrical ramp parameter target value to derive said ramp target signal, responsive to said monitored current value output and to a predetermined overcurrent threshold value to derive a said stop input when said monitored current value output exceeds said predetermined overcurrent threshold value, responsive to said monitored voltage value output and to a predetermined overvoltage value to derive a said stop signal when said monitored voltage value input exceeds said predetermined overvoltage value, and responsive to said start input, said ramp threshold signal and to said time interval of application input for deriving said stop input at the termination of said time interval of application;

said control assembly being responsive to said first channel monitored current value output, said first channel monitored voltage value output and to said predetermined load impedance value for deriving a first channel designated fault signal when said first channel monitored current value output and said first channel monitored voltage output represents a said impedance not corresponding with said predetermined load impedance, said control assembly being responsive to said second channel monitored current value output and said second channel monitored voltage value output and to said predetermined load impedance value for deriving a second channel designated fault signal when said second channel monitored current value output and said second channel monitored voltage output represents a said impedance not corresponding with said predetermined load impedance;

said control assembly further comprising a display assembly providing first and second perceptible indicia in the presence of said first channel designated electrode fault signal, and in the presence of said second channel designated electrode fault signal; and said control assembly being responsive to said second electrode designated monitor current value output, said second electrode designated monitored voltage output, and to said predetermined load impedance value for deriving a second electrode designated fault signal when said second electrode designated monitored current value output and said second electrode designated monitored voltage output represents an impedance not corresponding with said predetermined load impedance value, and said display assembly provides third perceptible indicia in the presence of said second electrode designated fault signal.

9. The apparatus of claim 8 including:

a d.c. offset detector assembly responsive to said electrical excitation outputs for providing a d.c. term value output; and said control assembly is responsive to said d.c. term value output and to a predetermined d.c. term limit of value effective to avoid iontophoresis to derive a said stop input when said d.c. term value output exceeds said predetermined d.c. term limit.

* * * * *